(12) United States Patent
Mirsky et al.

(10) Patent No.: US 6,261,606 B1
(45) Date of Patent: Jul. 17, 2001

(54) NATURALLY EXTRACTED AND SYNTHETIC HYPOGLYCEMIC OR HYPOLIPIDEMIC COMPOSITIONS

(75) Inventors: Nitsa Mirsky, Nofit; Anat Aharoni, Haifa; Sherbel Sussan, Tarshicha; Alon Margalit, Tivon, all of (IL)

(73) Assignee: Natural Compounds, Ltd., Tivon (IL)

( * ) Notice: Subject to any disclaimer, the term of this patent is extended or adjusted under 35 U.S.C. 154(b) by 0 days.

(21) Appl. No.: 09/395,534

(22) Filed: Sep. 14, 1999

(51) Int. Cl.[7] ............... A01N 65/00; A61K 35/78
(52) U.S. Cl. ........................... 424/725; 424/779
(58) Field of Search .................. 530/304, 417, 530/305, 413; 210/635, 656, 198.2; 424/725, 779

(56) References Cited

U.S. PATENT DOCUMENTS 5,059,329 * 10/1991 King ................................ 210/656

* cited by examiner

Primary Examiner—Jon P. Weber
Assistant Examiner—Patricia A. Patten
(74) Attorney, Agent, or Firm—Rashida A. Karmali

(57) ABSTRACT

Compositions having hypoglycemic and/or hypolipidemic activity are isolated from natural sources including yeast and Saltbush (Atriplex halmus). In addition, synthetic chromium complexes were prepared. Compositions possessing hypoglycemic and/or hypolipidemic activity with or without chromium containing natural and synthetic compounds are formulated for use in animals and humans. Methods for use of the compositions alone, or in combination with antioxidant agents, for regulating glucose and lipid levels in diabetes, cardiovascular diseases, inflammatory and cell proliferative diseases and in skin conditions, are presented.

4 Claims, 19 Drawing Sheets

NATURALLY EXTRACTED AND SYNTHETIC HYPOGLYCEMIC OR HYPOLIPIDEMIC COMPOSITIONS

The present invention is directed to processes of isolating purified compositions with or without chromium containing compounds, from a variety of natural sources including, but not limited to, a yeast strain *S. carlsbergensis*, or *S. cerevisiae*, or any commercial source of yeast extract; or from the Saltbush, *Atriplex halimus*, growing in the Negev Desert near the Dead Sea and other arid areas in the middle east. The invention also comprises production of synthetic sources of chromium, including, but not limited to chromium gluconate, chromium sulfate, chromium-cysteine, chromium-N-acetyl cysteine, chromiumn-glutathione, chromium acetate, chromium citrate, chromium ascorbate or chromium tartarate. The invention is also directed to formulations with or without chromium containing natural compounds or the synthetic chromium complexes, which specifically regulate glucose tolerance, glucose and lipid metabolism, insulin action, and metabolic activities in mammals who may be at an enhanced risk for or having a diabetic condition or cardiovascular diseases. In the practice of the method of treating diabetes, compositions containing the chromium complexes or the natural compositions with or without chromium containing compounds are used to regulate the diabetes related metabolic disregulation without general cytotoxic effects.

1. BACKGROUND OF THE INVENTION

Chromium (Cr) has been known as an essential trace element in animal and human nutrition. Cr deficiency may result in various symptoms including increased concentrations of circulating insulin, elevated blood glucose and cholesterol, decreased insulin receptor number, elevated triglyceride and free fatty acid levels and reduced high-density lipoprotein (HDL) cholesterol levels. These metabolic abnormalities, in general, are associated with risk for and/or incidence of diabetes. Moreover, chromium levels in most organs decline with age and in diabetics the chromium levels are even lower-than in other healthy adults. Anderson, R. A., Clin. Physiol. Biochem. 4: 31–41 (1986).

Malnutrition associated with Cr deficiency brings an impaired glucose tolerance. However, inorganic Cr compounds are poorly absorbed by the gut, whereas organic Cr components are well absorbed in the body. Glucose Tolerance Factor (GTF) is an organic complex of chromium present in several natural sources, the richest among them is Brewer's yeast. GTF was found to improve glucose tolerance in 50% of elderly patients with impaired glucose tolerance after two months of treatment. Despite these effects, the structure of GTF has not been identified as of yet. Several naturally occurring organic Cr compounds have been proposed to serve as GTF, for example, a partially purified cationic Cr compound extracted from yeast, soluble in water and has an absorption spectrum at 260nm, or the low-molecular-weight Cr-binding substance isolated from mouse or rabbit liver or bovine colostrum which has anionic properties. These organic Cr compounds have heretofore been used as crude extracts and the properties of their individual components remain uncharacterized. Evans, G. W. et al., Biochem. Biophys. Res. Commun. 50:718–722 (1973).

Hwang et al (U.S. Pat. No. 4,985,439) attempted to purify the Glucose Tolerance Factor from autolyzed brewer'yeast, and claimed that the active fraction is a quinoline derivative. King, S. (U.S. Pat. No. 5,108,610) also tried to isolate and purify a material possessing Glucose Tolerance Factor activity from eukaryotic cell mass, and claimed that the active material is dithiochrome. In addition, some patents describe a number of synthetic Cr compounds, (Furman C. S. et al, U.S. Pat. No. 5,266,560; Jensen N. L., U.S. Pat. No. 5,194,615; Wong Y., U.S. Pat. No. 5,536,863 Evans G. W., U.S. Pat. No. 5,087,624 and U.S. Pat. No. 4,315,927; Hwang D. et al, U.S. Pat. No. 4,985,439). Some patents describe chromium picolinate as a hypoglycemic chromium compound (U.S. Pat. No. 5,087,623; U.S. Pat. No. 5,087,624; and U.S. Pat. No. 5,175,156). The present invention is directed to development of improved processes to isolate natural compositions, with or without active and stable organic Cr compounds, as well as having hypoglycemic and/or hypolipidemic activity, from natural sources including, but not limited to, Brewer's yeast and Saltbush plant.

The present invention relates to compositions having hypoglycemic and/or hypolipidemic activity with or without natural or synthetic chromium compounds for application to individuals at risk for or suffering from diabetes, CVD, and cell proliferative diseases by regulation of metabolic abnormalities and/or inhibition of metabolic abnormalities within the target cells. In the practice of the invention, the natural or synthetic chromium compounds can be applied to supplement traditional pharmaceutical, hormonal and/or nutritional therapies for diabetes.

Diabetes mellitus is a disease of metabolic disregulation, notably of glucose metabolism, and long-term vascular and neurologic complications. Diabetes has several clinical forms, the two major forms being insulin-dependent diabetes mellitus I (IDDM) and the non-insulin-dependent diabetes mellitus II (NIDDM). IDDM is rare, affecting one in 250 persons in the United States, where approximately 10,000 to 15,000 new cases are reported each year. Data suggest that the incidence of IDDM is increasing in Europe, where the highest prevalence is found in northern Europe, for example, more than one in every 150 Finns develop IDDM by 15 years of age. LaPorte, R. et al., in Diabetes in America, $2^{nd}$ ed. Ed M. Harris, National institutes of Health, Bethesda, Md. NIH Publication No 95–1498, 1995.

NIDDM is common, with an overall prevalence of 6.6 percent in the United States. NIDDM has become one of the most frequent chronic diseases in most industrialized nations and the projected prevalence for the next decade is 10 percent. 600, 000 new cases are reported each year and one half of the NIDDM population are unaware of their disorder. The increase in the prevalence of NIDDM in the United States is commonly attributed to an aging population that is also increasingly obese and sedentary. The prevalence of NIDDM among persons older than 65 years exceeds 18 percent, and compared with normal-weight individuals, obese people with a body mass index greater than 30, are at 10 to 20 times greater risk for NIDDM. Although genetic and immunologic markers for IDDM have been identified, they are not enough nor sensitive enough to be used to define IDDM or distinguish IDDM and NIDDM. Harris, M. I., et al., Diabetes 36: 523 (1987); Bennett, P. H., et al., in International Textbook of Diabetes, ed Alberti KGMM, et al., John Wiley & Sons Ltd UK 1992, p148.

2. SUMMARY OF INVENTION

In accordance with the invention, improved processes of isolating from natural sources, compositions having hypoglycemic and/or hypolipidemic activity, with or without chromium containing natural extracted compounds are provided for use in individuals and animals at risk for or suffering from diabetes CVD and other cell proliferative diseases. The natural sources used include, but are not limited to the yeast stains S carlsbergensis and S cerevisiae, and the Saltbush Atrirplex halimus growing in the Negev Desert near the Dead Sea and other arid areas in the middle east.

The present invention also provides processes to produce synthetic sources of chromium complexes including, but not limited to, chromium gluconate, chromium sulfate, chromium-cysteine, chromium-N-acetyl cysteine, chromium-glutathione, chromium acetate, chromium citrate, chromium ascorbate or chromium tartarate.

The present invention also provides methods for the synthesis of chromium complexes, which are pure and can be prepared in large quantities without possibility of contamination.

The present invention provides formulations having hypoglycemic and/or hypolipidemic activity, with or without chromium containing natural and synthetic compositions exhibiting GTF activity, for application in a variety of diseases or conditions including, glucose intolerance, hyperlipidemia, hypercholesterolemia, obesity, vascular and fibrotic proliferative diseases, skin lesions, diabetic neuropathy or to regulate abnormal metabolic processes associated with diabetes, or CVD.

The present invention provides formulations having hypoglycemic and/or hypolipidemic activity, with or without chromium containing natural and synthetic complexes which can be applied in combination with an effective amount of one or more additional antioxidants including vitamin C, vitamin E, reduced glutathione, manganese, beta-carotene, ergothioneine, zinc, selenium, cysteine, N-acetyl cysteine, methionine or 2-mercaptoethanol.

According to an additional aspect of the present invention, there is provided a method to regulate glucose metabolism, insulin activity, lipid metabolism and lipoprotein lipase activities by applying formulations having an effective amount of hypoglycemic and/or hypolipidemic activity, with or without chromium containing natural and synthetic chromium compositions.

According to yet another aspect of the invention, there is provided a method to regulate glucose metabolism, insulin activity, lipid metabolism and lipoprotein lipase activities by applying formulations having hypoglycemic and/or hypolipidemic activity, with or without chromium containing natural and synthetic chromium compositions in combination with an effective amount of one or more antioxidants including vitamin C, vitamin E, reduced glutathione, manganese, beta-carotene, ergothioneine, zinc, selenium, cysteine, N-acetyl cysteine, methionine or 2-mercaptoethanol.

The present invention also provides a method to regulate glucose metabolism, insulin activity, lipid metabolism and lipoprotein lipase activities, including application of formulations of chromium containing natural and synthetic chromium compositions in combination with a conventional therapeutic regimen including hormonal therapy or one or more pharmaceutical agents.

The present invention is based on the discovery of improved processes to produce more purified compositions having hypoglycemic and/or hypolipidemic activity, with or without chromium containing natural extracted compounds.

The present invention is based on the discovery of improved processes to produce synthetic compositions of chromium compounds.

The present invention is also based on the discovery of improved formulations of chromium containing natural and synthetic compositions which exhibit a greater potency in regulating metabolic abnormalities associated with diabetes and obesity.

It is also the object of the present invention to provide formulations having hypoglycemic and/or hypolipidemic activity, with or without chromium containing natural and synthetic compositions which are effective when used alone or in combination with antioxidants or conventional therapies.

It is an object of the present invention to provide methods for the synthesis of chromium complexes which exhibit GTF activity.

It is also an object of the present invention to provide methods for the synthesis of chromium complexes which are pure and can be prepared in large quantities without possibility of contamination.

It is another object of the present invention to provide methods for prevention and treatment of diabetes-related abnormalities in glucose and lipid metabolism, or insulin and lipoprotein lipase activities.

Still other objects and advantages of the invention will in part be obvious and will in part be apparent from the specification.

The invention accordingly comprises the several steps and the relation of one or more of such steps with respect to each of the others, and the product embodying properties, which are adapted to effect such steps and methods, all as exemplified in the following detailed disclosure, and the scope of the invention will be indicated in the claims.

3. BRIEF DESCRIPTION OF THE DRAWINGS

For a fuller understanding of the invention, reference is had to the following description taken in connection with the accompanying drawings, in which:

FIG. 1 is a diagram illustrating the individual steps in the process by which the chromium containing natural compositions are extracted and purified from yeast strain or yeast extract. These steps include: a) mixing of crude yeast preparation with a chloroform/methanol/water solvent, b) separation of the aqueous phase, c) mixing of the aqueous fraction with ethanol, and d) isolating the active sediment fraction, e) mixing the sediment with methanol f) ultrafiltration of methanol eluate g) collection of the active fraction below 1000 dalton.

FIG. 2 is a diagram illustrating individual steps in the process by which the chromium containing natural compositions are extracted and purified from the Saltbush. These steps include: a) preparation of a crude mixture of Saltbush, b) mixing of the crude preparation with a chloroform/methanol/water solvent, c) separation of the aqueous phase, d) mixing of the aqueous phase with ethanol, e) separation of the active component in the eluate, f) mixing of the active component with methanol, and separation of the eluate containing the active fraction.

FIG. 3 is an elution profile of 100% methanol elute from Saltbush on preparative HPLC $C_{18}$ column. The mobile phase used: $H_2O$+1% ammonium acetate; 100% $H_2O$; a gradient between 100% water to 100% acetonitrile. Several peaks were observed at 250 nm. The activity of the isolated fractions was measured in yeast fermentation assay. Fraction 1 was found to be most active. Fractions 6–7 showed also high activity whereas all the other isolated fractions were inactive.

Figure 14:
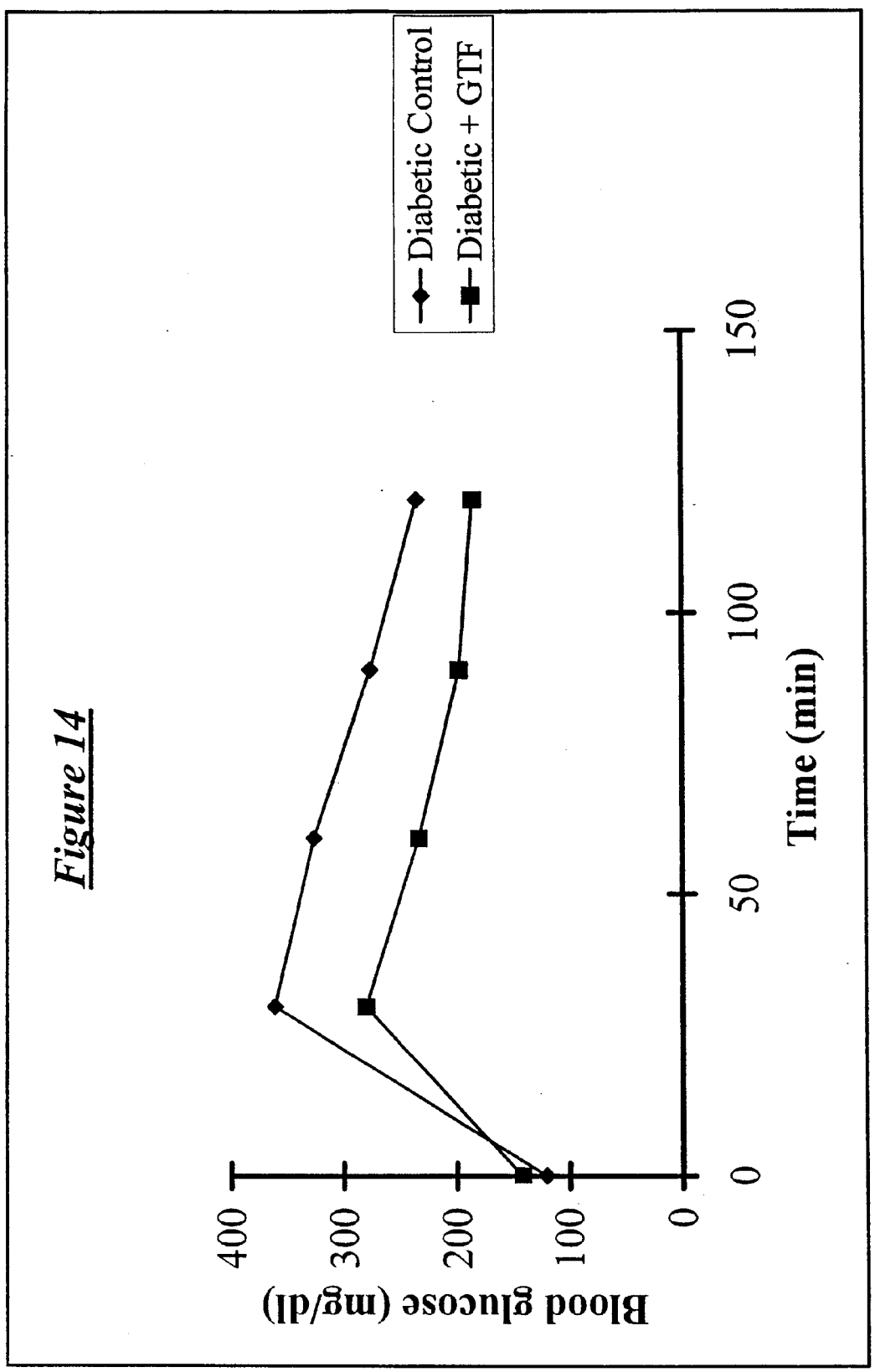

FIG. 14 describes oral glucose tolerance test in diabetic rats which were either untreated or which were given an oral single dose of 140 ng Cr/rat of chromium containing natural compositions extracted from yeast. Diabetes type I was induced in rats with streptozotocin.

Figure 15:
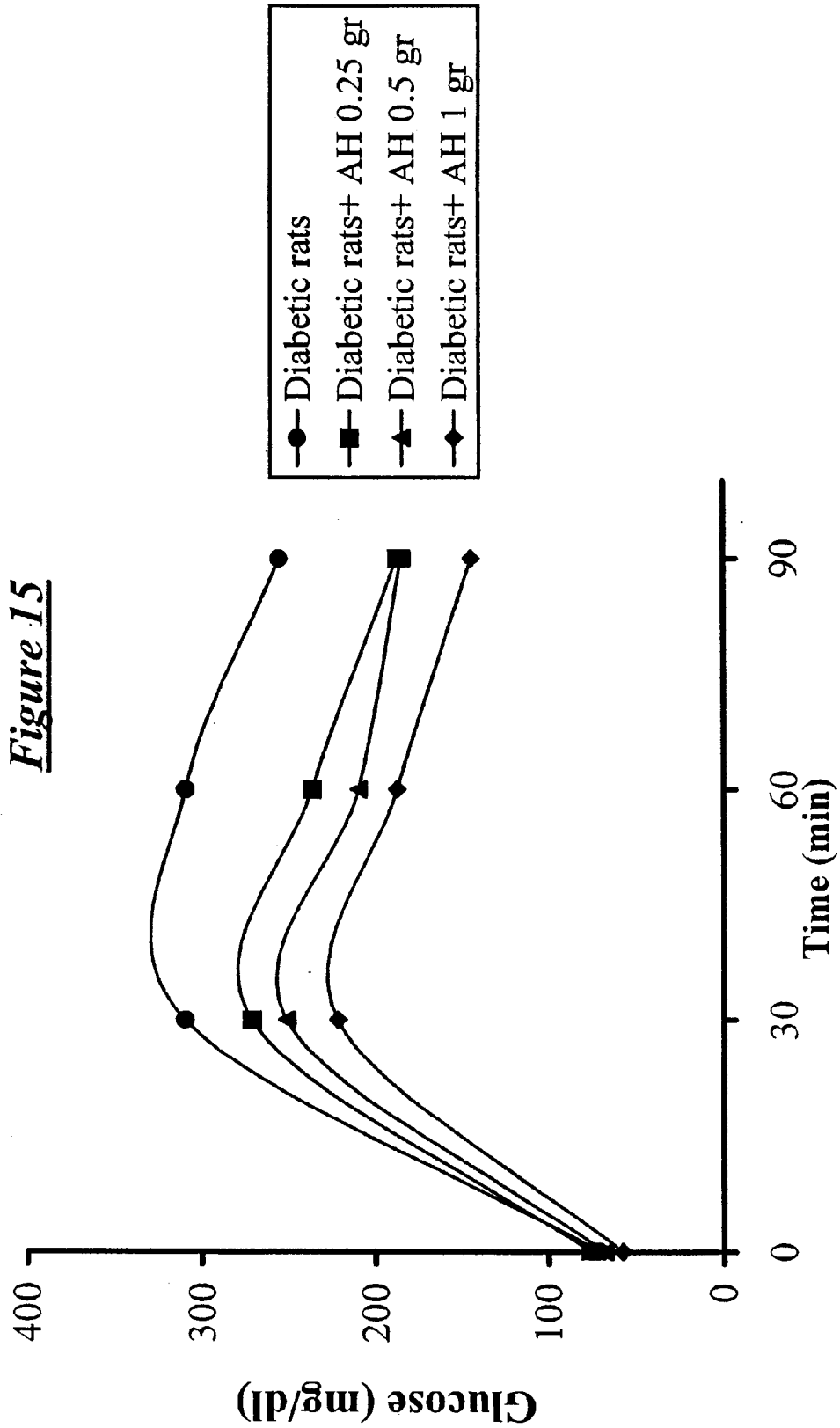

FIG. 15 describes glucose load in diabetic rats which were either untreated or which were given an oral single dose of 0.25, 0.5 or 1 g/rat of natural active compositions extracted from Saltbush. Diabetes type I was induced in rats with streptozotocin.

Figure 16:
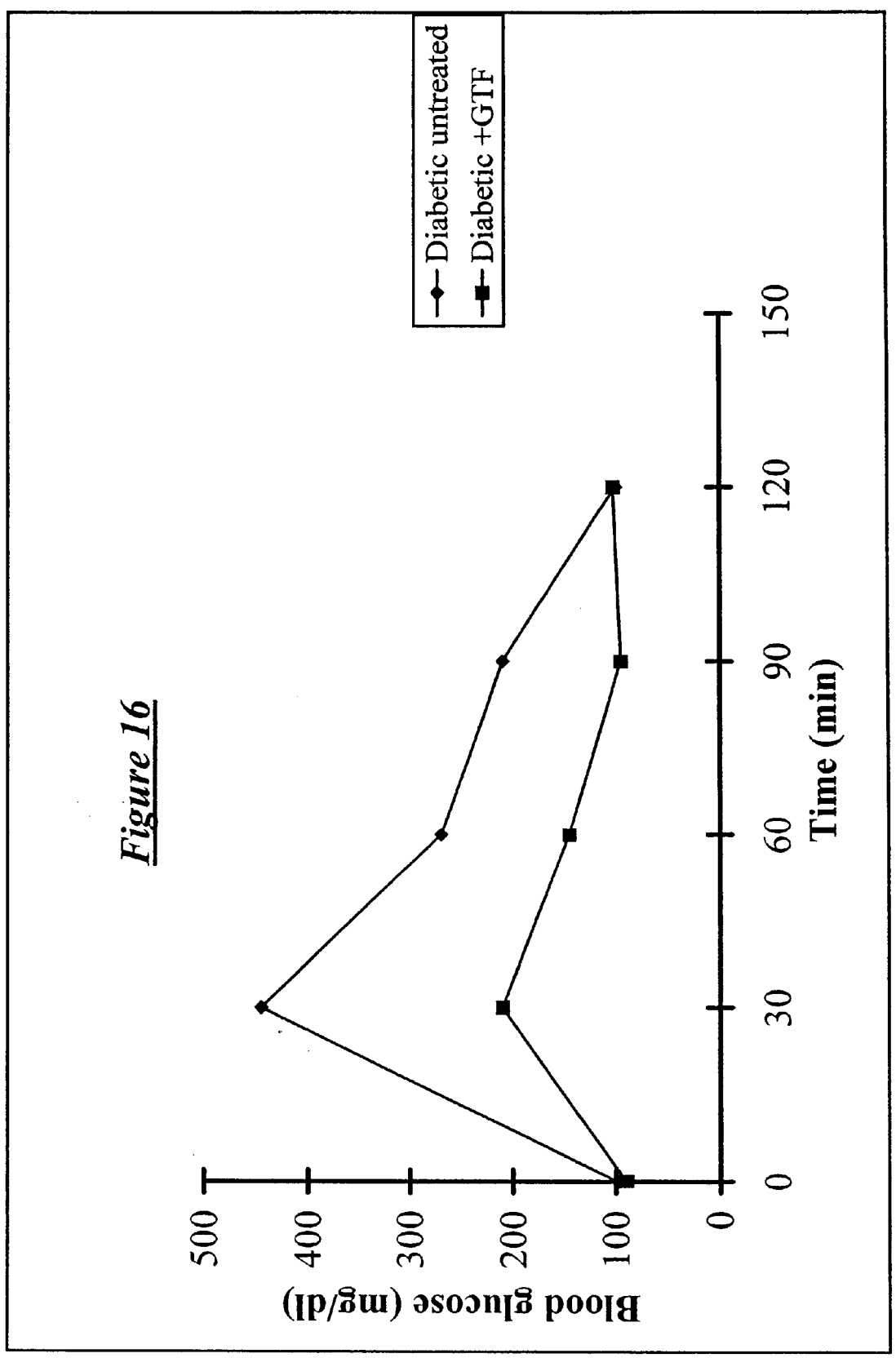

FIG. 16 describes glucose tolerance in diabetic spiny mice (Acomys russatus) suffering from diabetes type II which were either untreated or given a single oral dose of chromium containing natural composition extracted from yeast (200 ng Cr/animal).

Figure 17:
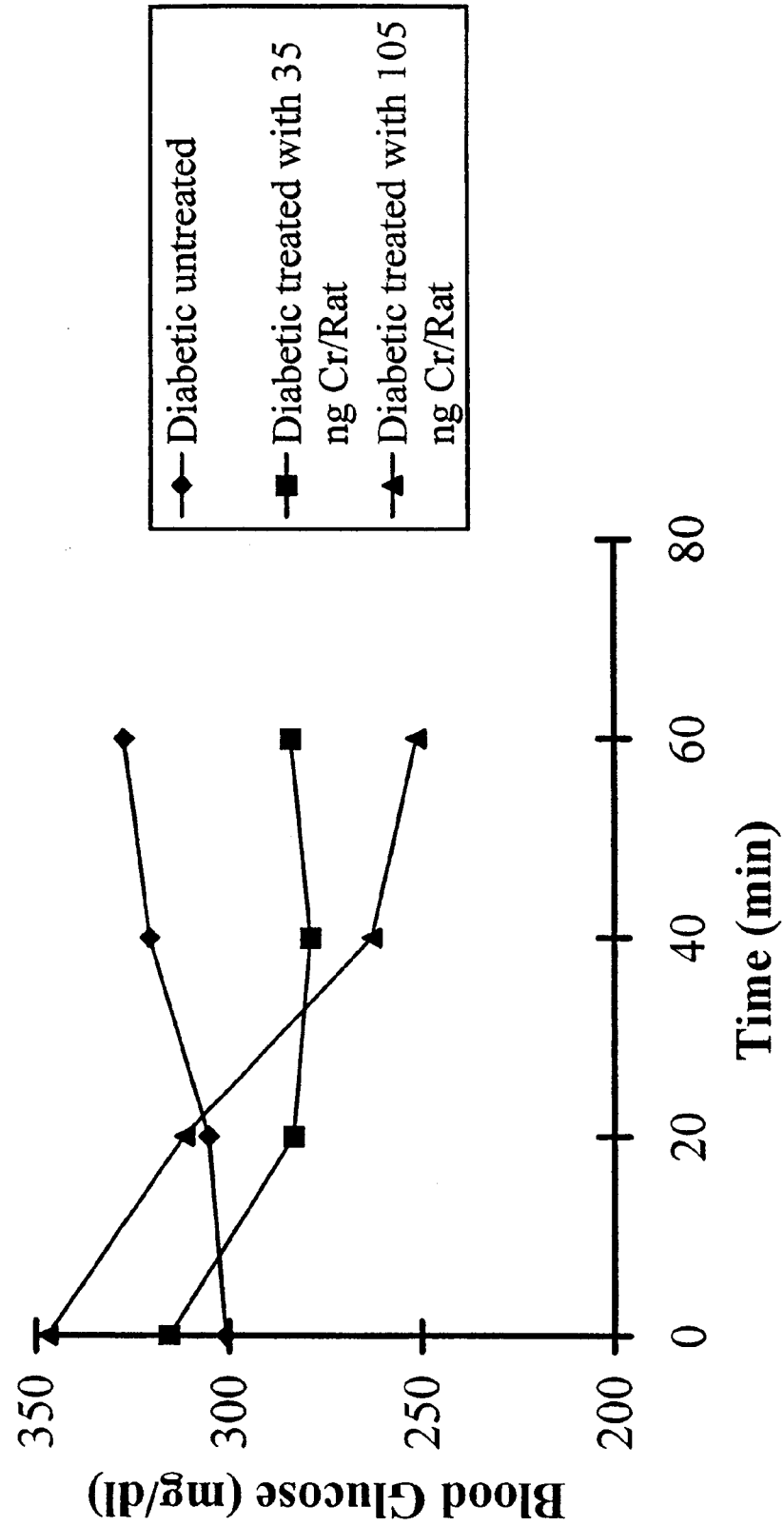

FIG. 17 describes glucose tolerance in diabetic Sand rat (Psammomys Obesus) suffering from diabetes type II, which were either untreated or which were given a single oral dose of chromium containing natural composition extracted from Saltbush.

Figure 18:
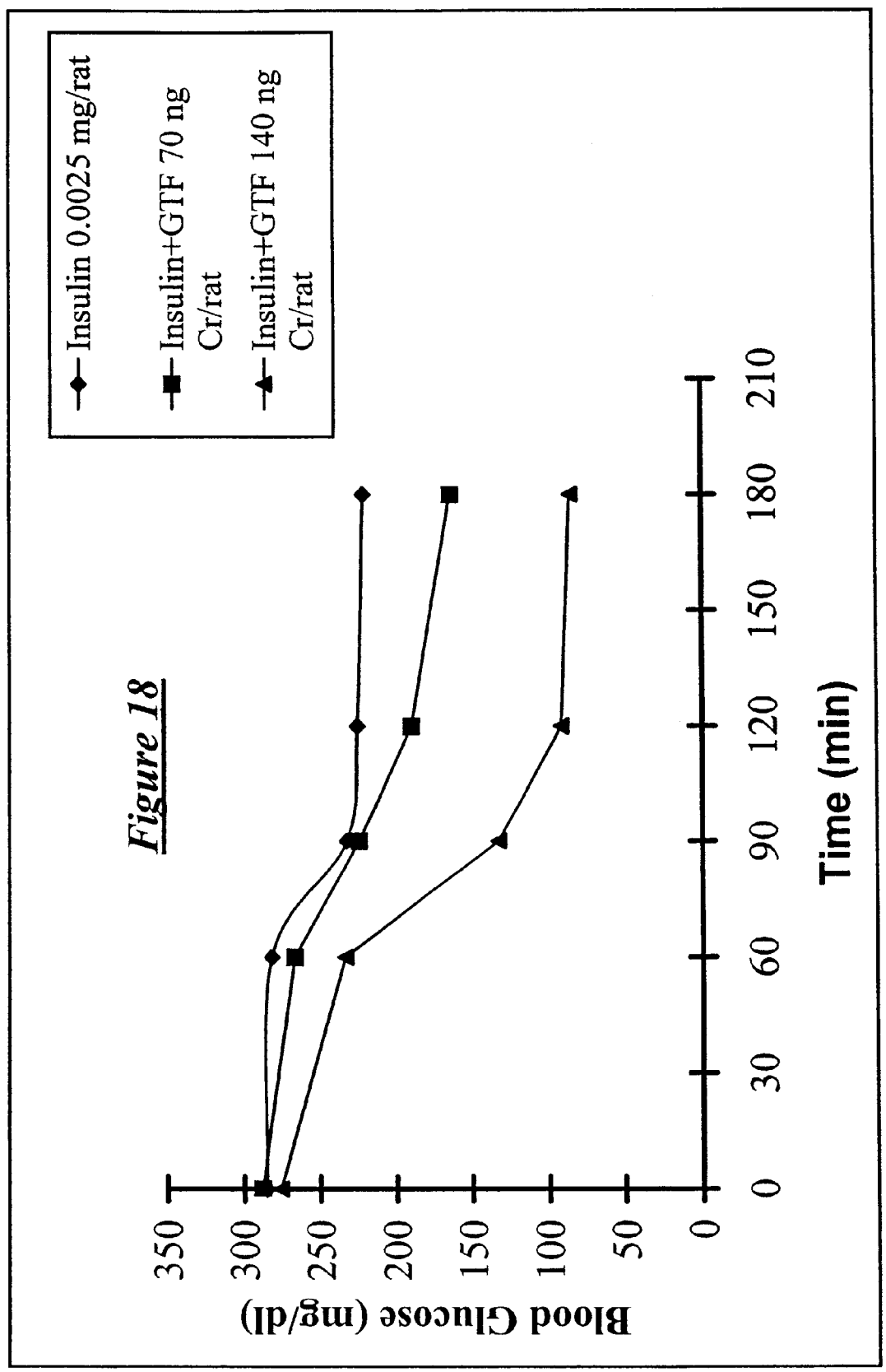

FIG. 18 describes the effect of chromium containing natural composition extracted from yeast on the activity of marginal levels of insulin in diabetes type I in rats.

Figure 19:
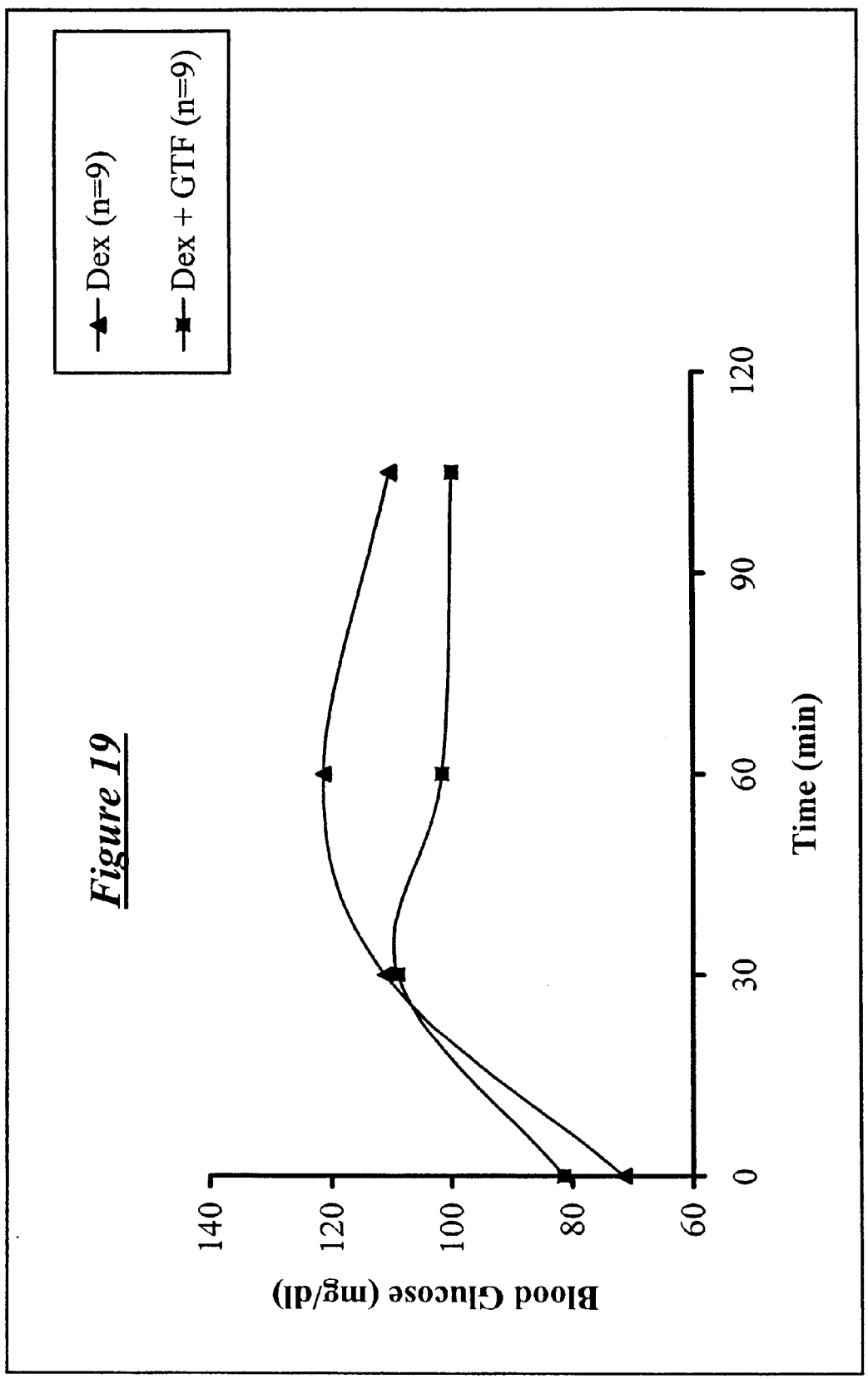

FIG. 19 describes blood glucose levels in diabetic rats which were either untreated or which given an oral single dose of chromium containing natural composition extracted from yeast. Diabetes was induced by steroid treatment for several days.

4. DETAILED DESCRIPTION OF THE INVENTION

The present invention generally pertains to reveal processes, formulations and methods for use of natural compositions having hypoglycemic and/or hypolipidemic activity, with or without chromium, from a variety of natural sources including, but not limited to, a yeast strain *S. carlsbergensis* or *S. cerevisiae*, or any commercial source of yeast extract, or Saltbush Atriplex halimus, growing in the Negev Desert near the Dead Sea or other areas in the middle east. The present invention is also directed to processes of making, formulations and methods for use of synthetic chromium complex compositions. The methods are directed to regulate abnormalities related to diabetes, cell proliferative diseases and/or vascular diseases. The present invention also provides formulations and methods for inducing cellular and biochemical changes in cells and tissues that show functional deficit in diseases including diabetes, cell proliferative diseases and/or vascular diseases, and in obesity by altering lipase activity.

4.1 Diabetes The two major forms of diabetes are insulin-dependent diabetes mellitus (IDDM) of type I, and the non-insulin-dependent diabetes mellitus (NIDDM) of type II. A third form of diabetes is induced by steroid treatment.

The definition of diabetes implies both abnormal glucose levels and long-term vascular and neural complications. Patients with impaired glucose tolerance are at high risk for retinopathy or nephropathy but are at greater risk for macrovascular disease. In addition, 30 to 50 percent of patients with impaired glucose tolerance develop NIDDM within 10 years after diagnosis. Jarrett, J. J. et al., Diabetologia 22:79 (1982). Thus, intervention at this pre-diabetic stage may prevent subsequent development of NIDDM.

In a non-diabetic person with normal sensitivity to insulin, insulin secretion is adequate to maintain normal glucose homeostasis by promoting glucose uptake by the liver and muscles and by inhibiting hepatic and muscle glucose output. In the fasting state, hepatic glucose output maintains normal serum glucose levels, and in the fed state, glucose is stored by the muscles and liver. Glucose levels stimulate normal insulin secretion.

However, in individuals with insulin resistance and impaired glucose tolerance, pancreatic islets hypertrophy and insulin secretion increases to maintain adequate glucose uptake in the liver and muscle. However, glucose uptake by muscle is also impaired after eating and glucose flux from the liver may begin to increase. When individuals who are insulin resistant decompensate i.e., when impaired glucose tolerance progresses to diabetes, beta cell function wanes, causing increased hepatic glucose output and fasting hyperglycemia, and muscle uptake further decreases. Chronically elevated glucose levels further increase insulin resistance and decrease insulin secretion, a condition thus, termed glucotoxicity. Correction of glucose levels partly reverses the deleterious effect of hyperglycemia.

Impaired glucose uptake by muscle may be secondary to abnormal glucose transport, decreased glucose phosphorylation (which is the rate-limiting step in glucose metabolism in the muscle), impaired glycogen synthesis, unsuppressed glycogenolysis or gluconeogenesis or a combination of these conditions. When insulin requirements and insulin delivery are mismatched, the results are abnormal glucose, lipid and protein metabolism. Insulin causes its myriad cellular effects by binding to specific high-affinity receptors. Thus, the natural and synthetic compositions of the present invention which regulate glucose levels as well as influence insulin activity provide novel products and methods for treatment of diabetic patients.

In non-diabetic subjects in the fed state, insulin levels are increased and glucagon levels are decreased. This results in the storage of triglycerides in adipose tissue, glycogen synthesis and thus the storage of glucose in the liver and muscle, and the storage of amino acids in muscle protein. When subjects with either IDDM or NIDDM are deficient in insulin, they have a relative excess of glucagon. In this condition, the catabolic effects of insulin deficiency and glucagon excess predominate, resulting in glycogenolysis and gluconeogenesis and impaired muscle uptake of glucose leading to hyperglycemia. Increased lipolysis causes an increased flux of free fatty acids to the liver where under the influence of glucagon, they are converted to ketones. In NIDDM, endogenous insulin levels are usually sufficient to suppress ketogenesis. Muscle uptake of amino acids and protein synthesis are decreased. In addition, increased hepatic synthesis of triglycerides and decreased triglyceride clearance result in increased levels of circulating triglycerides. Thus, the natural compositions of the present invention which regulate triglyceride levels, provide novel and safe products and methods for the control of triglycerides in diabetic patients.

In NIDDM, more than 85 percent of patients are obese and at increased risk of coronary vascular disease. The relative risk of cardiovascular disease for diabetic women is increased even more than for diabetic men. Numerous risk factors for cardiovascular disease accompany NIDDM in addition to obesity, e.g. hypertension, dyslipidemia (low HDL and high VLDL with dense LDLs). The incidence of peripheral vascular and cerebrovascular disease is also increased in patients with diabetes. The combinations of peripheral neuropathy and peripheral vascular disease results in a risk of amputations in the dieabetics that is 40 times greater than in the non-diabetics. Thus, the natural and synthetic compositions of the present invention which inhibit lipid peroxidation and modulate the oxidation of LDL, modulate arachidonic acid metabolism by inhibiting cyclooxygenase 2 (COX-2) and exhibit antioxidant, anti-inflammatory and antiplatelet activities, provide novel products and methods for treatment of vascular and proliferative diseases.

Thirty three percent of adults over the age of 20 in the United States are obese. Obesity is loosely defined as an excess of fat over that needed to maintain health. Many factors are involved in the pathogenesis of obesity, including the control of feeding behavior, mechanisms of fat storage, the components of energy intake and expenditure, and genetic and psychological influences. Surplus nutrients are converted to triglycerides and stored in adipocytes. The storage is regulated by the enzyme lipoprotein lipase. The lipoprotein lipase activity varies in different parts of the body and fat deposits in the highly active sites are associated with higher cholesterol levels and other cardiac risks. The natural and synthetic compositions of the present invention are useful in regulating obesity by regulating functions including, but not limited to, reducing cholesterol levels, regulating lipoprotein lipase activity and triglyceride synthesis and exerting antioxidant effects in obesity.

Chromium (Cr) has been known for more than three decades as an essential trace element needed for animal and human nutrition. Rats fed a Cr-deficient diet developed glucose intolerance, in addition to elevated levels of blood glucose and cholesterol, decreased growth, and a reduced life span. Serum and tissue Cr concentrations in old or diabetic animals are lower than in young and healthy animals. Chromium is the only element known in humans to decline in most organs with age. Its concentrations in people with diabetes are even lower than in other healthy adults. Guthrie E.. In: Langard S, editor. Biological and environmental aspects of chromium. Amersterdam: Elsvier Biomedical Press; 117–47 (1982).

Patients on long-term total parenteral nutrition developed severe symptoms of glucose intolerance, which could be partially reversed by intravenous administration of $CrCl_3$ of very high concentrations. Jeejebhoy KH, et al., Am J Clin Nutr 30: 531–38 (1977). However, inorganic Cr compounds are poorly absorbed by the gut, whereas organic Cr compounds are better absorbed in the body.

The glucose tolerance factor (GTF) is a dietary agent that is required for normal glucose tolerance in animals and man. The earliest detectable symptom of GTF deficiency in animal, is an impairment of glucose tolerance, whereas more severe deficiency leads to glycosuria, fasting hyperglycemia, impaired growth, decreased longevity, elevated serum cholesterol, increased incidence of aortic plaques, and corneal opacities. R. A. Anderson, and W. Mertz, Trends in Biochem. Sci. 2, 277–279 (1977). Despite this important role of the naturally occurring Cr compound, GTF has not been characterized heretofore.

One of the major problems related to the field of GTF, is the lability of the partially purified GTF preparations and the synthetic complexes. This lability, can partially explain the complexity of the subject , and the fact that in spite of the long time since the material was discovered, its exact composition and structure have not been determined.

Two natural sources for active organic chromium compounds are described in the present invention. Brewer's yeast sources are the richest source for active Cr material. The Saltbush is another traditional origin for active hypoglycemic material known among the Arabs living in the Negev Desert and near the Dead Sea in Israel.

The Salt-bush (*Atriplex halimus L., Chenopodiaceae*) is a large branched shrub, grown in arid and semi arid habitats in the Mediterranean and the Saharo-Arabian deserts. It is especially common in inundated saline depressions, and around oases of the Jordan valley. It is also commonly found in the Negev mountains, the Moav mountains and the Sinai peninsula (Flora Palaestina Part One, PP 143–154, Michael Zohary, ed. Goldberg Press, Jerusalem, 1966). Saltbush leaves are the exclusive source of food for the fat sand rat (Psamonys obesus; Gerbillinae), a relative large gerbillid rodent found in the Saharo-Arabian deserts. Frenkel G. & Kraicer P F., Life Sci. 11: 209–222, 1972. When fed on normal laboratory chow, or a high energy diet, sand rats develop severe hyperglycemia within 2 months (Schmidt-Nielsen K & Haines HB., Science 143: 689–690, (1964). This effect was reversed when press juice, water extract or dialysate from salt-bush leaves were added to the chow diet. (Aharonson Z., Shani J. & Sulman F G., Diabetologia 5: 379–383,( 1969). However, no attempts to isolate the active hypoglycemic factor(s) from saltbush leaves have been reported heretofore.

4.2 Formulations and Dosage

Compositions with or without chromium containing natural and synthetic compounds of the present invention may be formulated into pharmaceutical preparations for administration to animals and humans for a variety of effects including, but not limited to, glucose regulation, triglyceride, cholesterol and fatty acid regulation, lipid peroxide production and arachidonic acid metabolism regulation, diabetes mellitus, cardiovascular diseases, inflammatory diseases, eczema, skin warts, psoriasis or arthropathy.

Many of the compositions containing natural and synthetic compositions with or without chromium may be provided as compounds with pharmaceutically compatible counter ions, a form in which they may be soluble.

The natural and synthetic compounds may be administered intravenously, intraperitoneally, subcutaneously, intramuscularly, intrathecally, orally, rectally, topically, or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed contains.

Dosages for oral administration of chromium containing natural and synthetic compositions for human use range from 25 to 1000 microgram Cr/day, commonly 50 to 500 microgram Cr/day, and typically from 50 to 100 microgram Cr/day, or 0.5–50 $\mu$g Cr/Kg body weight.

Dosage amount and interval may be adjusted individually to provide plasma levels of the active moiety which are sufficient to maintain the antidiabetic and other favorable metabolic effects.

Alternatively, one may administer the compound in a local, rather than oral manner, for example, via injection of the compound directly into the target site, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Example of such carriers or excipients include, but are not limited to, calcium carbonate, calcium phosphate, various sugars, starches, cellulose derivatives, gelatin, and polymers such as polyethylene glycols.

Furthermore, one may administer the agent in a targeted drug delivery system for example, in a liposome coated with a tissue specific antibody. The liposomes will be directed to and taken up selectively by the target tissue.

In cases of local administration or selective uptake, the effective local concentration of the chromium compound may be related to plasma concentration.

Figure 1:
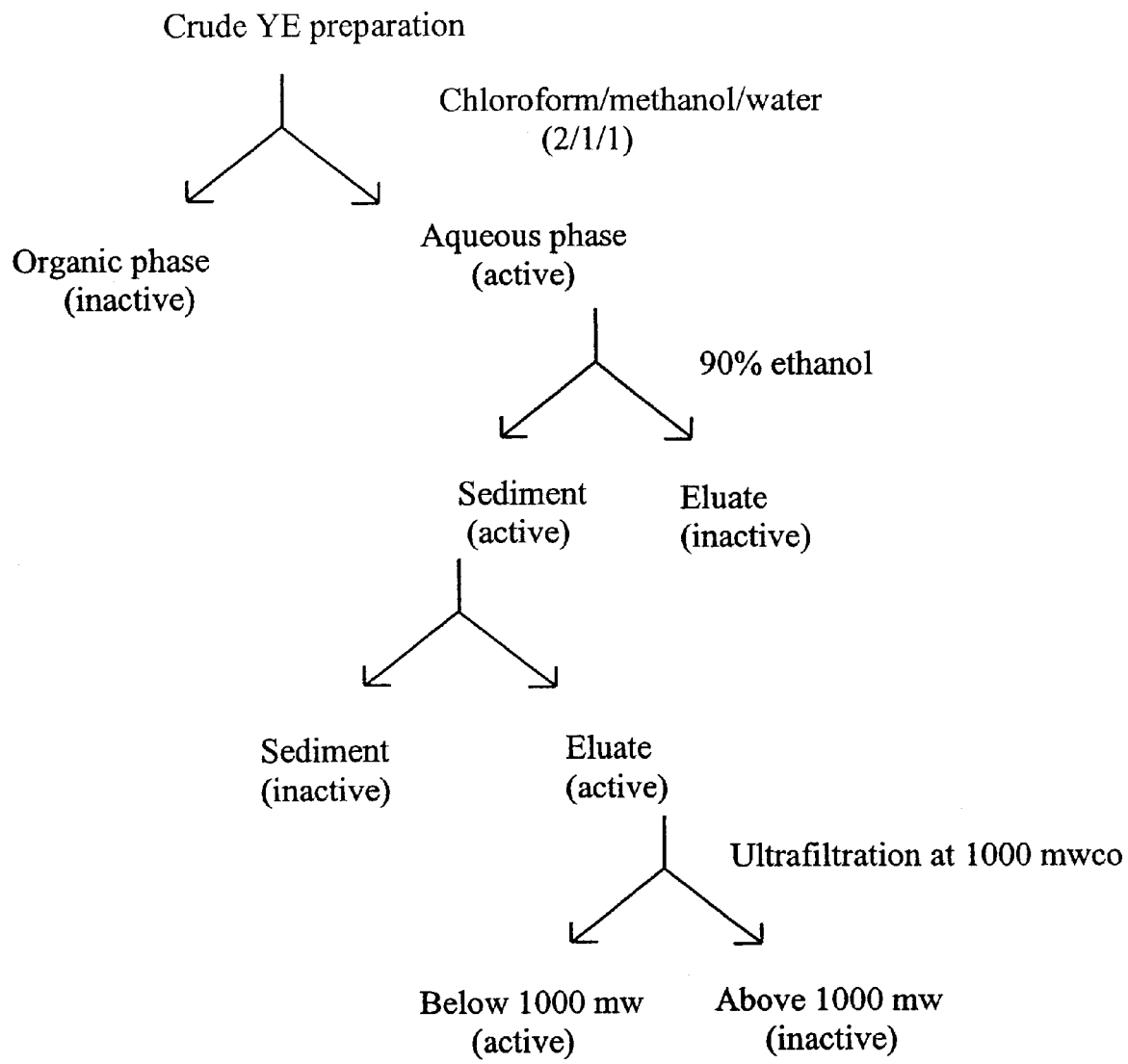

5. EXAMPLES 5.1 Extraction and isolation of
Chromium containing natural
compounds from yeast FIG. 1 describes the procedure for obtaining chromium containing natural fractions from the yeast strains S. carlsbergensis or S. cerevisiae or commercial yeast extracts. When using yeast cells the cell walls can be broken by autolysis or mechanical rupture. When using yeast extract, 50 grams of granulated yeast extract were dissolved in 100 ml distilled water by stirring for 30 min. An equal volume of methanol (analytical grade, Frutarom, Il) and 2 volumes of chloroform (analytical grade, Frutarom; Il) were added and sequentially mixed with the yeast extract suspension. The mixture was left for 2 hrs. until good phase separation was evident. Most of the lower chloroform phase was removed in separation funnel, and the rest of the mixture was centrifuged at 10,000 rpm, 10 min, at room temperature (Sorvall, Conn., USA). Good separation was apparent, resulting in a lower clear chloroform phase, upper dark aqueous phase and intermediate white solid material. This procedure was repeated until no solid precipitate was observed. GTF activity of each fraction was tested in yeast fermentation assay described below in Section 5.4. Only the aqueous phase was active.

The upper aqueous phase was collected and the rest was discarded. The aqueous preparation was concentrated by Rotavapor (Buchi, Gr) and re-suspended in 50 ml water in 500 ml Erlenmeyer bottle. The suspension was mixed with 450 ml absolute ethanol (analytical grade, Frutarom, Il) for ethanol precipitation. Most of the particulate matter was seedimented to the bottom of the bottle. The rest was sedimented by centrifugation at 10,000 rpm, 10 min, RT. Two types of sediments were observed: a dark viscous sediment that stuck to the bottom and a powdery white material that remained in the suspension. Each of the fractions was collected, recovered in water and tested for GTF activity in the yeast fermentation assay. Only the dark sediment retained the activity, while the non-sedimented compounds were found inactive.

The active preparation was concentrated to 50 ml and further purified by mixing it with 450 ml methanol for methanol 90% precipitation. A dark precipitant was apparent. The eluate and sediments were collected, dried, resuspended in 50 ml water and screened in the yeast fermentation assay. Only the methanol 90% eluate retained GTF activity.

The active preparation was sequentially filtered by ultrafiltration membranes with molecular weight cut-off at 3000 and 1000 dalton (Diaflo, Amicon, Mass., USA). Each fraction was tested for GTF activity in the yeast fermentation assay. The fractions below 1000 molecular weight were active.

The active fraction has cationic properties: It binds strongly to the cation exchange column Dowex 50W×8, but not to anion exchange column DE-52.

5.2 Extraction and isolation of
chromium containing natural
compounds from Saltbush.

Figure 2:
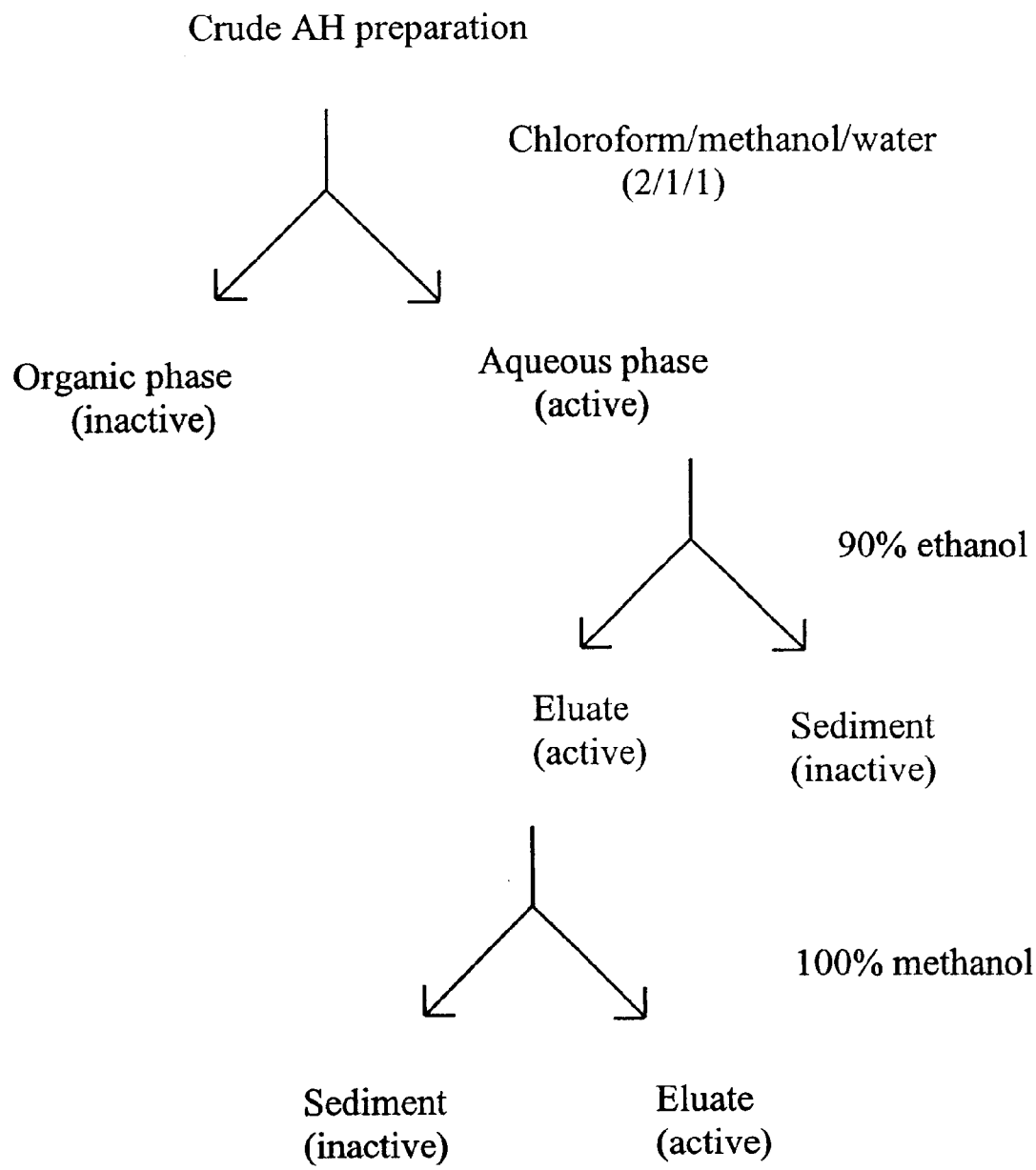

FIG. 2 describes the procedure for obtaining purified chromium complex fractions from Saltbush. Hundred grams of dried Saltbush (Atriplex. halimus) leaves were placed in a 2 1 beaker, and mixed with 500 ml of water. The preparation was boiled for 1 hour, cooled down, chopped to very fine pieces by a laboratory blender, and boiled again for additional 3 hours. The preparation was then left to cool down and filtered over a screen fabric to remove solid debris.(a) The aqueous preparation was concentrated to 100 ml volume, mixed with an equal volume of methanol (analytical grade, Frutarom, Israel) and mixed vigorously. Then, 2 volumes of 100 ml of chloroform (analytical grade, Frutarom, Israel) were added sequentially and mixed with the rest. The mixture was transferred to a separation funnel and left for 2 hours until good phase separation was evident. The lower chloroform phase was removed. The rest was collected and centrifuged at 10,000 rpm, 10 min, RT (Sorvall, Conn. USA). The upper aqueous phase, the lower organic phase and the intermediate solid phase were collected and tested for biological activity in the yeast fermentation assay (described below in Section 5.4). Only the aqueous phase was biologically active and processed forward. The rest was discarded.

The aqueous phase was concentrated to 50 ml volume under Rotavapor (Buchi, Gr), mixed with 450 ml ethanol and left at 4° C. overnight. A dark precipitant was sedimented to the bottom of the bottle. The eluate, which had a light brown color was collected, dried and dissolved in water. The precipitate was also dissolved in water. Both fractions were tested for biological activity in the yeast fermentation assay. The sediment was inactive. The eluate showed high biological activity. The active ethanol eluate was dried completely under Rotavapor and dissolved in 100% methanol. The precipitate had a pale salty crystal appearance, and was biologically inactive. The eluate had a light brownish color and was very active in the yeast fermentation assay.

Figure 3:
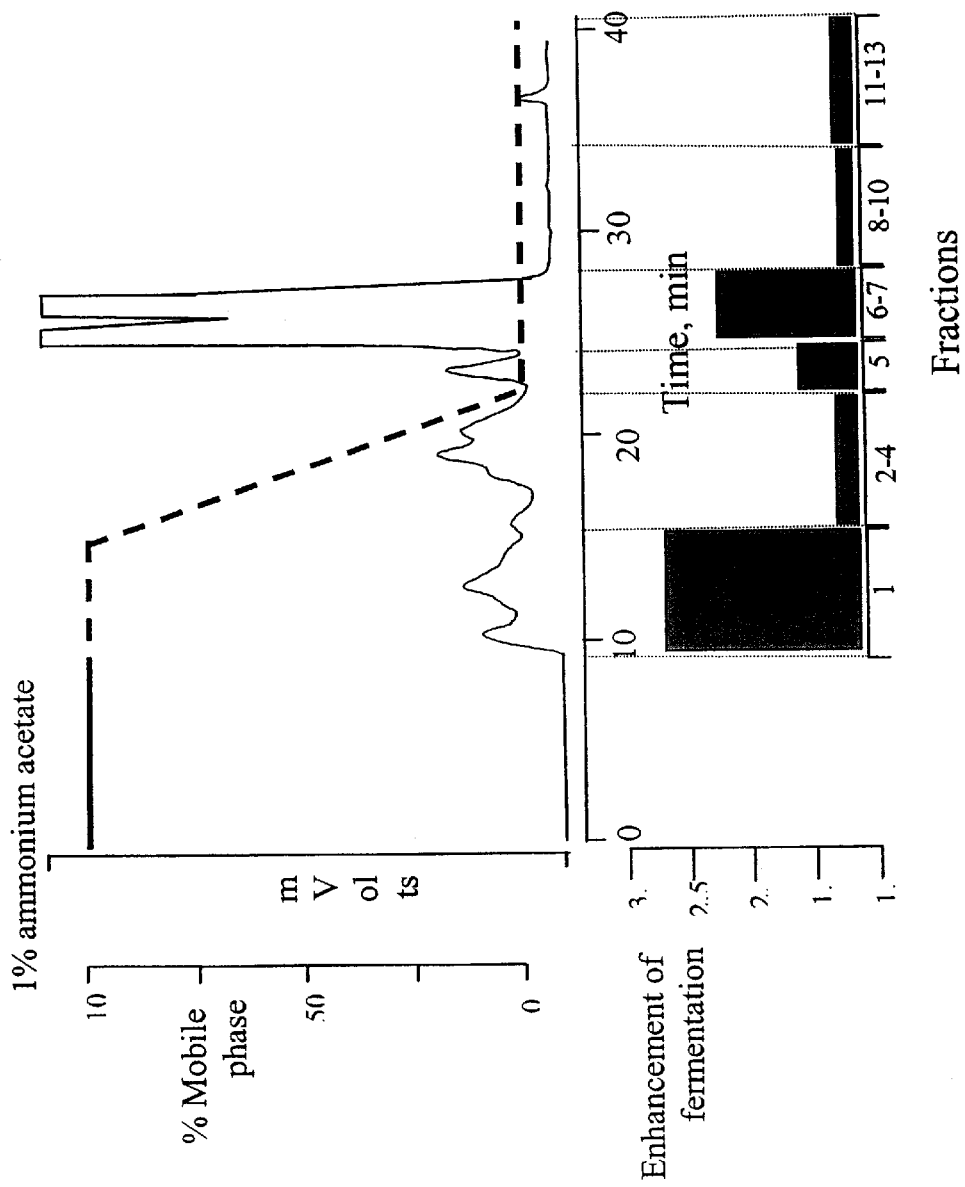

The active fraction has cationic properties. It binds to cation exchange column Dowex 50 W×8, but not to anion exchange column DEAE -52. The active fraction was filtered through Sep-Pak C18 Column (Waters). The flow-through and the water wash were pooled together. The attached material was eluted with 100% methanol. The flow-through was found to exhibit biological activity. 100 $\mu$g of the active fraction were injected to preparative HPLC (FIG. 3) using the following mobile phase: 0–8 min, 100e% $H_2O$+1% ammonium acetate; 8–14 min, 100% $H_2O$; 14–25, from 100% $H_2O$ to 100% acetonitrile; 25–35, 100% acetonitrile. Several peaks were observed at 250 $\lambda$. Fractions were collected, and the ammonium hydroxide was removed. The dry material was re-suspended in 1 ml water and tested in the yeast fermentation assay at 1/20, 1/100 and 1/200 dilutions. The highest activity was observed in fraction 1. Fraction 6–7 were also found active. Fraction 5 had lower activity. All the other fractions were inactive.

Figure 4:
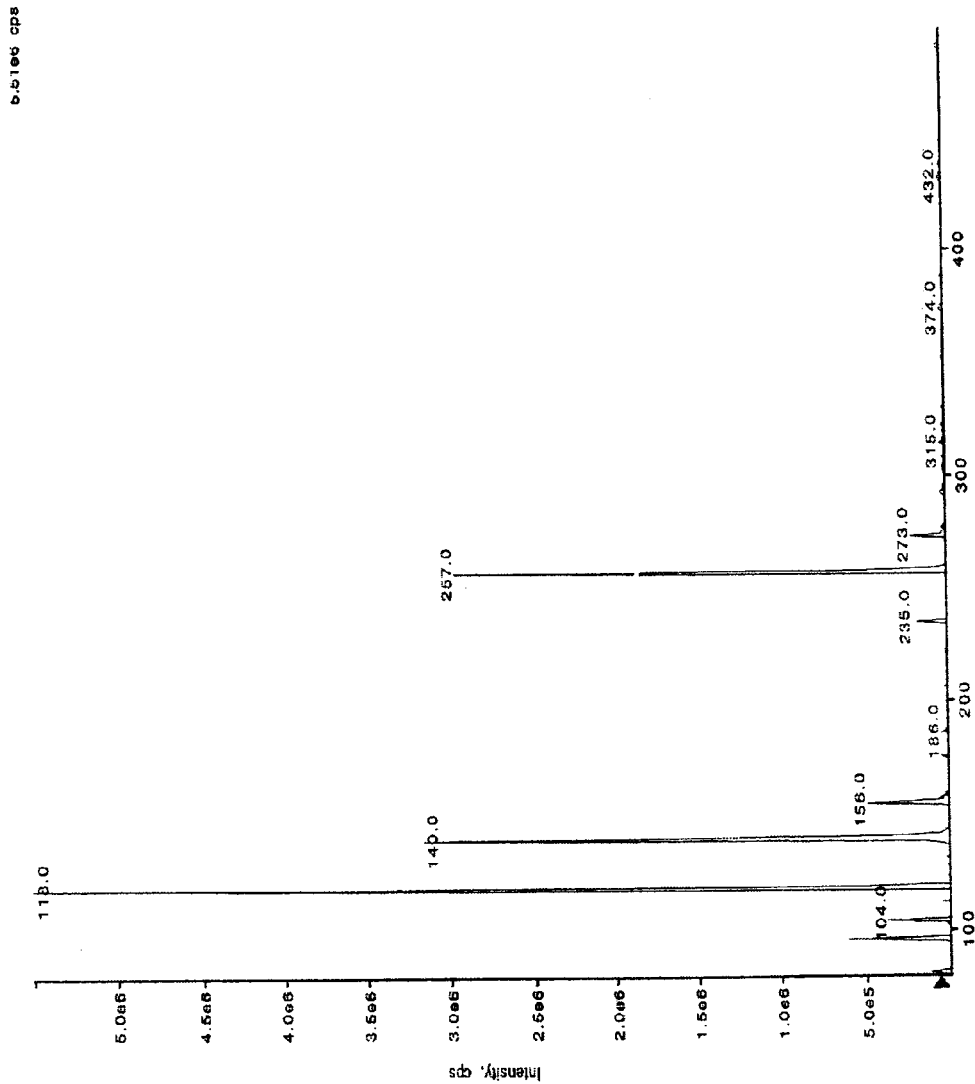
FIG. 4 is a Mass Spectra (negative ion mode) of Fraction 1, from Saltbush extract (Ah) eluted from HPLC, by electrospray mass spectrometry (EP-Sciex, EPI 2000).
Figure 5:
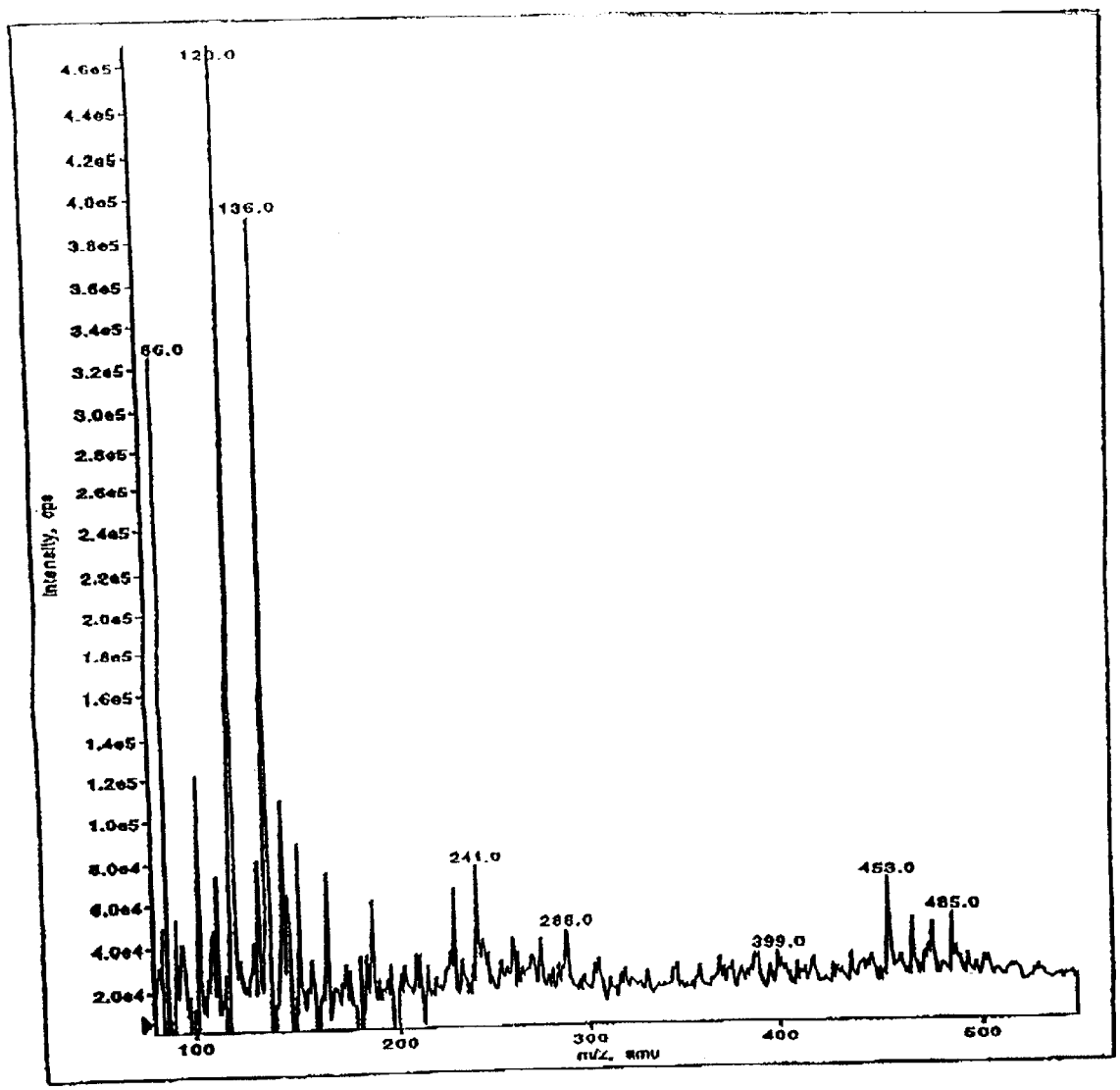
FIG. 5 is a Mass Spectra (negative ion mode) of Fractions 6–7, from Saltbush extract (Ah) eluted from HPLC, by electrospray mass spectrometry (EP-Sciex, EPI 2000).

Fractions 1 and 6–7 were analyzed by electro-spray Mass Spectrometer (Sciex EPI 2000, Perkin-Elmar, Toronto, ON. Canada), using positive mode (FIG. 4). In fraction 1, three major peaks were observed at m/z 257, 140 and 118. Minor peaks were observed at m/z 273, 235, 156 and 104. The masses at m/z 257, and 140 were originated from the mass at m/z 273. The mass at m/z 118 was originated from the mass at m/z 235. In fraction 6–7 (FIG. 5), two major peaks were observed at m/z 136 and 120, and three minor peaks at m/z 152, 103 and 86. No association between masses was found.

5.3 Preparation of Synthetic chromium
containing compositions

The method of synthesis of four members of the chromium complex family is described below:

Preparation of Chromium Ascorbate (Cr-Asc)- Half gram (1.85 mmole) of chromium chloride ($CrCl_3$) was dissolved in 30 ml of deionized water to get a green solution. 1.0 g (5.5 mmole) of ascorbic acid (Asc) dissolved in 40 ml of deionized water, was added to the solution. The pH of the reaction mixture was adjusted to 4.5 ($pK_{(Asc)}$=4.2), and the reaction mixture was stirred for 3 hours at 50° C. to get a dark green solution. The solution was concentrated in vacuum and the large volume of ethanol 90% was added to get a green sediment. UV-VIS Spectrum for Cr-Asc showed two main absorbance peaks at 263 and 592 nm.

Chromium Cmsteine (Cr-Cys) One gram (3.7 mmole) of chromium chloride ($CrCl_3$) was dissolved in 40 ml of deionized water to get a green solution. 2g (15 mmole) of cysteine (Cys) was dissolved in 40 ml of deionized water were added, and the reaction mixture was stirred for 2 hours at 40° C. until the solution turned violet.

The absorbance peaks for Cr-Cys are 410 and 550nm. The absorbance peaks for $CrCl_3$ are 440 and 630 nm. Cr-Cys is strongly bound to the cation exchange column Dowex 50X8.

Chromium-Glutathione (Cr-GSH)- One gram (3.7 mmole) of chromium chloride ($CrCl_3$) was dissolved in 40 ml of deionized water to get a green solution. 4.6 g (15 mmole) of glutathione (GSH) was dissolved in 40 ml of deionized water were added, the pH of the reaction mixture adjusted to 6, and the reaction mixture was stirred for 3 hours at 40° C. until the solution turned violet. The absorbance peaks for Cr-GSH are 410 and 550 nm.

Chromium N-Acetyl Cysteine (Cr-NAC)- One half gram (1.85 mmole) of chromium chloride ($CrCl_3$) was dissolved in 30 ml of deionized water to get a green solution. 1.5 g (9.2 mmole) of N-acetyl cysteine (NAC) was dissolved in 40 ml of deionized water were added, and the mixture was stirred for 3 hours at 40° C. until the solution turned dark green-blue.

The absorbance peaks for Cr-NAC are 425 and 575nm. Cr-NAC is a cationic complex and binds to the cation column Dowex 50X8.

Determination of chromium concentration

Chromium was determined by atomic absorption using graphite furnace. (Spectra Atomic Absorption model 300/400)

5.4 Assessing natural and synthetic chromium compounds activity in vitro by the Yeast fermentation assay 5.4.1 Enhancement of fermentation Rate by fractions derived from yeast.

Yeast strain carlsbergensis was used for the experiments.

The cells were kept on a solid chromium depleted medium that contained 6.7 g yeast nitrogen base, 20 g of glucose, and 18 g agar per liter. Cells were grown over night in a liquid medium without Cr. Yeast cells were harvested during stationary phase, washed twice and resuspended in 0.1 M phosphate buffer pH 5.7. An aliquot of $3 \times 10^8$ cells/ml was anaerobically incubated at 30° C. in Warburg vessels in the presence of 10 mM glucose and the examined fraction of GTF extracted from yeast. Enhancement of fermentation rate by natural or synthetic chromium compounds was measured.

TABLE 1

Enhancement of fermentation rate by fractions derived from yeast extracts (relative to control)

| | | Relative activity* | | |
|---|---|---|---|---|
| Fraction | total w (g) | 0.05 g/l | 0.1 g/l | 0.5 g/l |
| Yeast extract | 100 | 1.38 | 1.65 | 2.4 |
| Aqueous phase ($CHCl_3$/MeOH/$H_2O$) | 91 | 1.44 | 1.7 | 2.44 |
| Sediment, 90% EtOH | 61 | 1.55 | 1.8 | 2.63 |
| Eluate, 90% MeOH | 40 | 2.04 | 2.4 | 2.99 |

Figure 6:
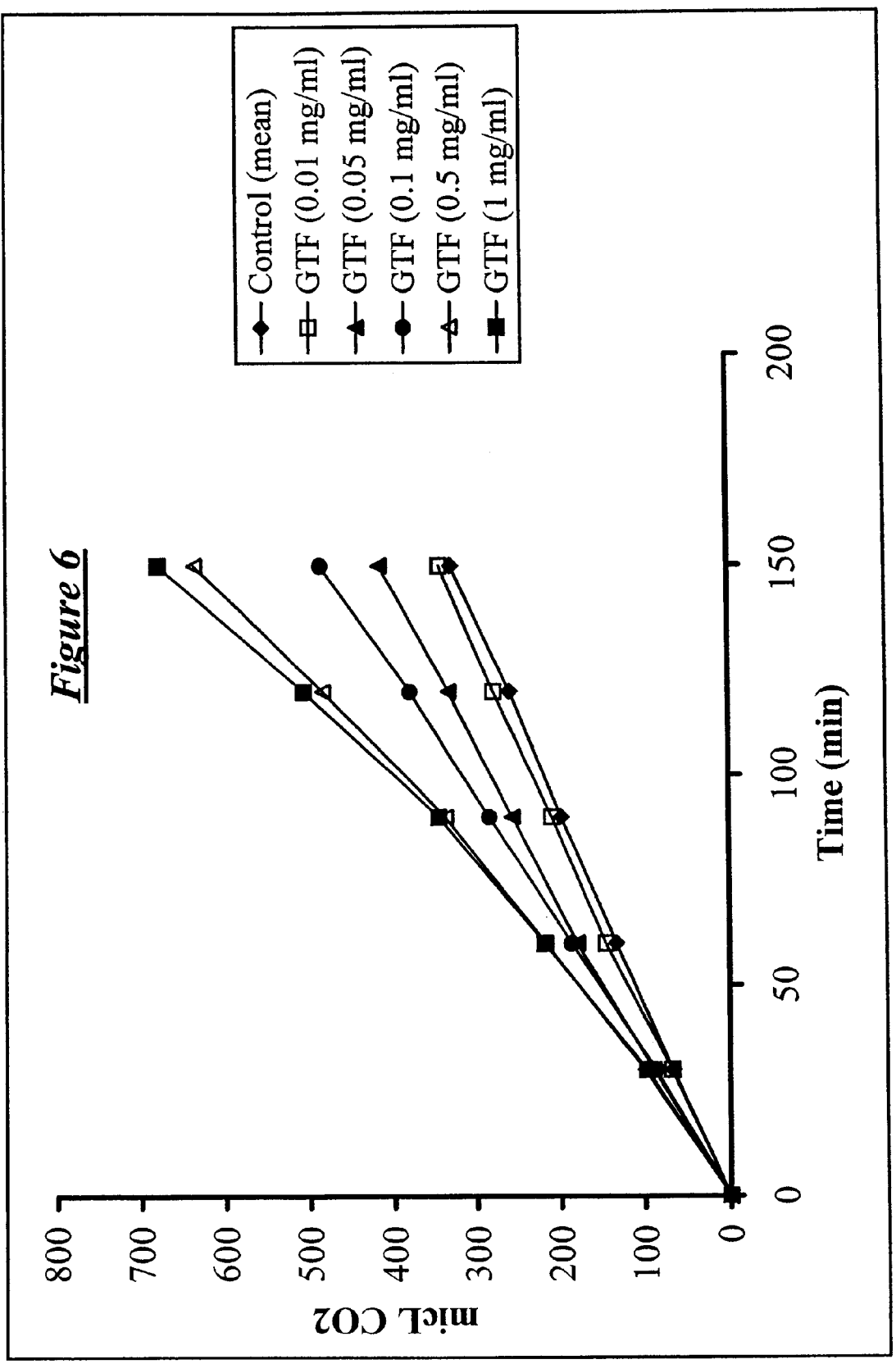
FIG. 6 is a diagram illustrating carbon dioxide production in yeast cells in chromium depleted medium and after addition of active fractions of natural compositions extracted and purified from yeast.

*The fermentation rate is the rate of $CO_2$ production ($\mu$mol/min) by yeast cells under anaerobic conditions at 30° C. The relative activity (the enhancement) is calculated according to the fermentation rate in the samples containing the tested fractions, divided by the rate of fermentation in the control. Table 1 and FIG. 6 show a dose-related enhancement of fermentation rate in all fractions of yeast extract, where the most active fraction is 90% methanol eluate.

*The fermentation rate is the rate of $CO_2$ production ($\mu$mol/min) by yeast cells under anaerobic conditions at 30° C. The relative activity (the enhancement) is calculated according to the fermentation rate in the samples containing the tested fractions, divided by the rate of fermentation in the control. Table 1 and FIG. 6 show a dose-related enhancement of fermentation rate in all fractions of yeast extract, where the most active fraction is 90% methanol eluate.

5.4.2 Enhancement of fermentation rate by fractions derived from the Saltbush (*Atriplex halimus*)

Yeast cells were grown over night in liquid medium without Cr. Yeast cells were harvested during stationary phase, washed twice and resuspended in 0.1 M phosphate buffer pH 5.7. An aliquot of $3 \times 10^7$ cells/ml was anaerobically incubated at 30° C. in Warburg vessels in the presence of 10 mM glucose and the examined fractions extracted from Saltbush.

TABLE 2

Enhancement of fermentation rate by fractions derived from Saltbush extract (relative to control)

| Fraction | total w (g) | Relative Activity* | | |
|---|---|---|---|---|
| | | 0.1 g/l | 0.5 g/l | 1 g/l |
| Dry leaves | 100 | — | — | — |
| Crude extract | 26.6 | 1.1 | 1.6 | 1.8 |
| Aqueous phase ($CHCl_3$/MeOH/$H_2O$) | 18.7 | 1.2 | 1.8 | 2.0 |
| Eluate, 90% EtOH | 3.2 | 1.5 | 1.9 | 2.2 |
| Eluate, 100% MeOH | 1.7 | 2.07 | 2.6 | 2.9 |

Figure 7:
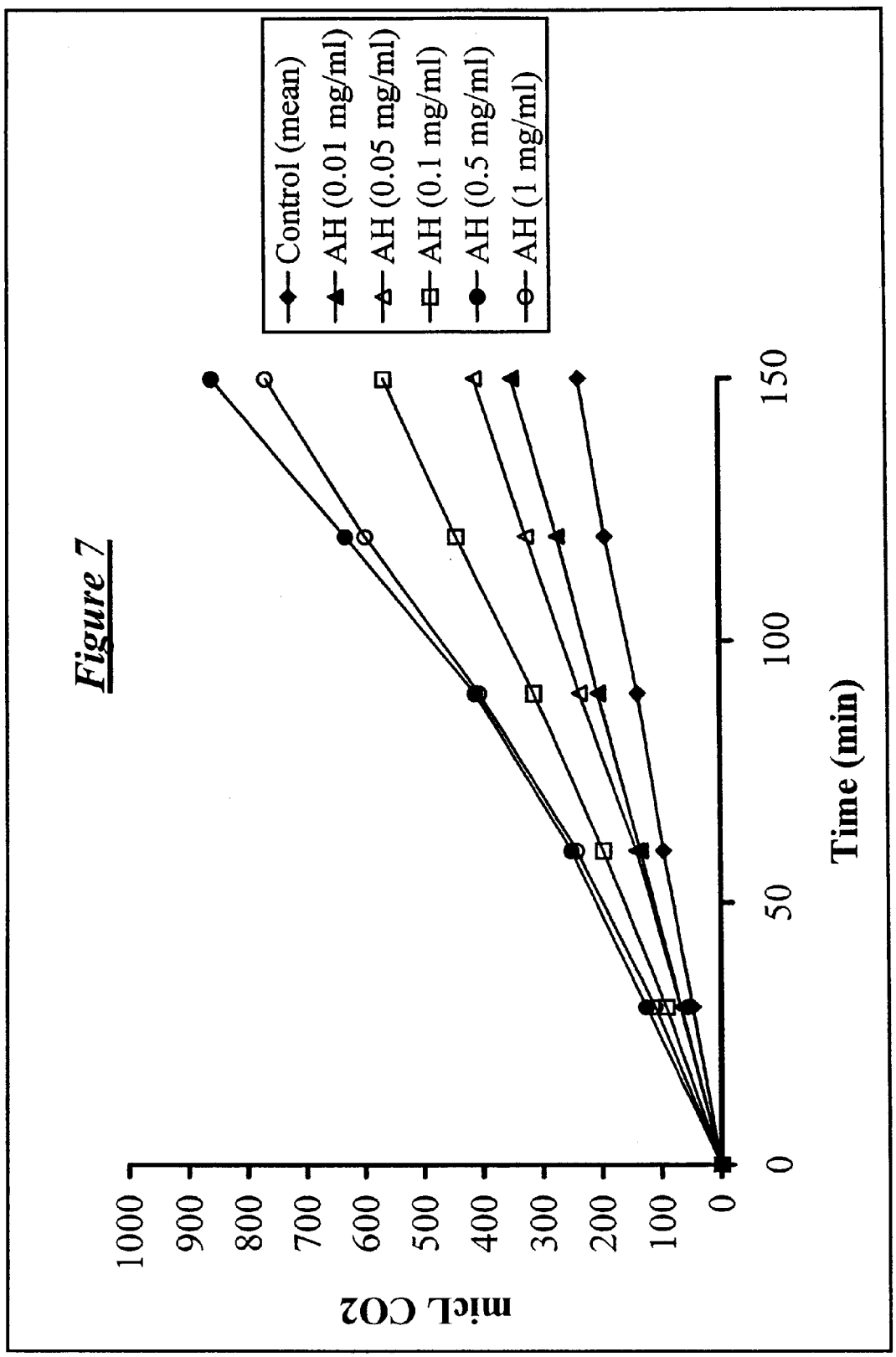
FIG. 7 is a diagram illustrating carbon dioxide production in yeast cells in chromium depleted medium and after addition of active fractions of natural compositions extracted and purified from Saltbush.

*Fermentation rate is the rate of $CO_2$ production ($\mu$mol/min) by yeast cells under anaerobic conditions at 30° C. The relative activity (the enhancement) is calculated according to the fermentation rate in the samples containing the tested fractions, divided by the rate of fermentation in the control. Table 2 and FIG. 7 show a dose-related enhancement of fermentation rate in fractions of Saltbush extract. where the most active fraction is 100% methanol eluate.

*Fermentation rate is the rate of $CO_2$ production ($\mu$mol/min) by yeast cells under anaerobic conditions at 30° C. The relative activity (the enhancement) is calculated according to the fermentation rate in the samples containing the tested fractions, divided by the rate of fermentation in the control. Table 2 and FIG. 7 show a dose-related enhancement of fermentation rate in fractions of Saltbush extract. where the most active fraction is 100% methanol eluate.

5.4.3 Activity of the synthetic chromium complexes in yeast fermentation assay:

The activity of the synthetic chromium complexes was examined in the yeast fermentation assay as described above. All the complexes were tested by adding samples of the subject complex, and measuring the rate of $CO_2$ production.

FIGS. 8–13 present dose dependent activity of "CrAsc", "Cr-GSH" and "Cr-NAC" in yeast fermentation assay.

"Cr-Asc" was found to be most active (FIGS. 8 and 9) with a typical saturation curve without any inhibition at high concentrations of the material, whereas high concentrations of "Cr-GSH" or "Cr-NAC" showed partial inhibition in yeast fermentation.

Figure 8:
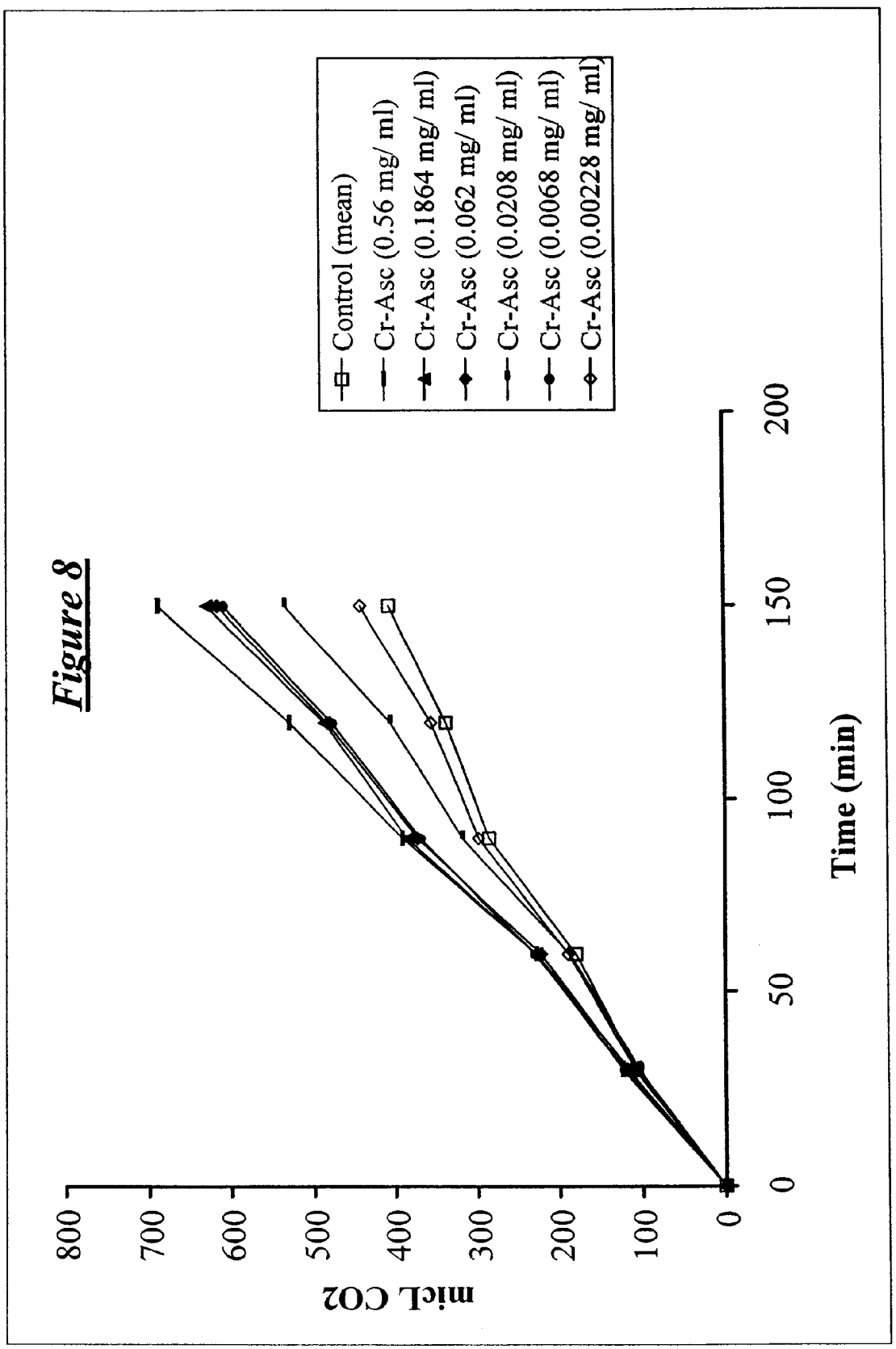
FIG. 8 is a diagram illustrating carbon dioxide production in yeast cells in chromium depleted medium and after addition of different concentrations of chromnium-ascorbate.
Figure 9:
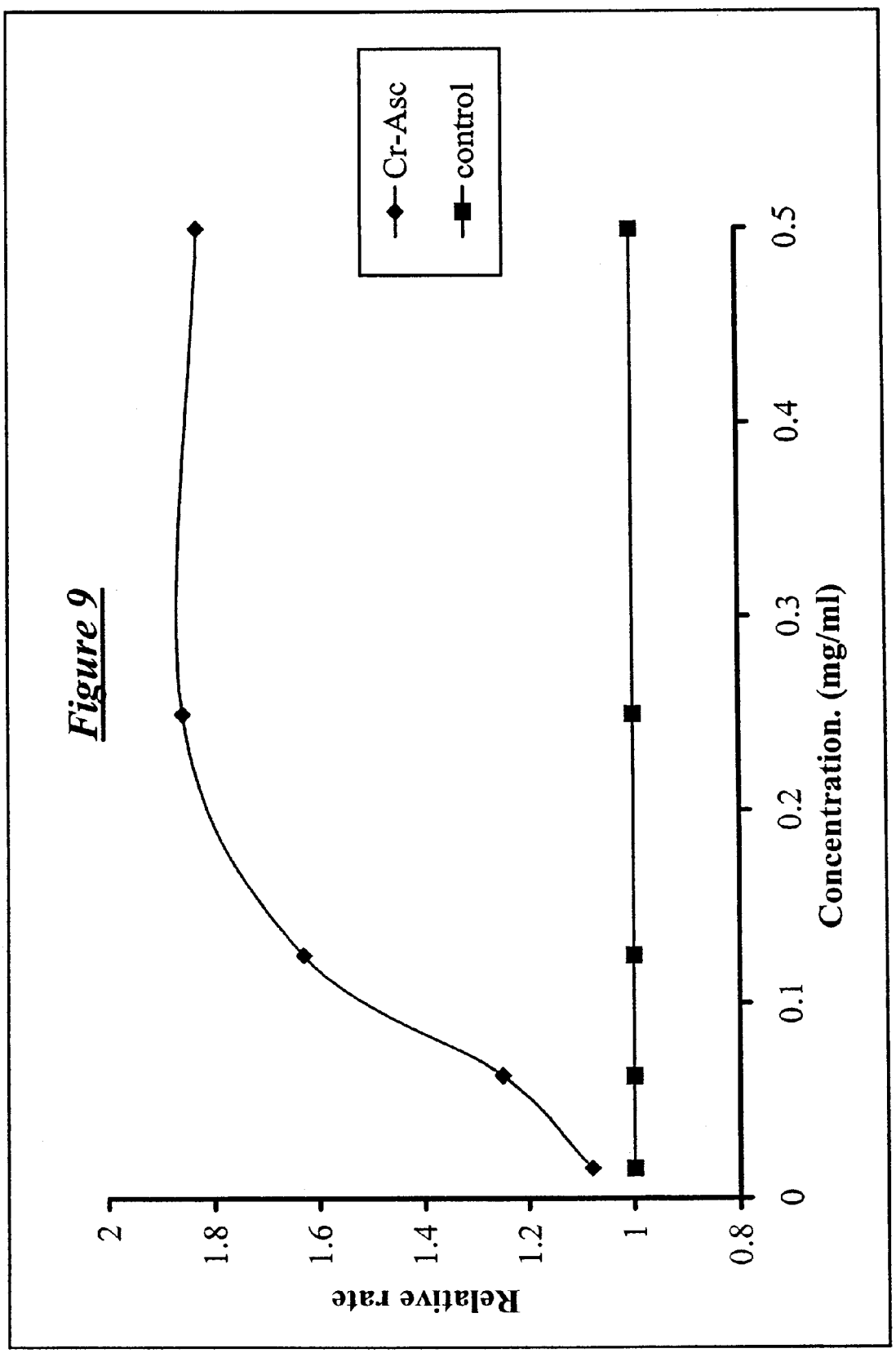
FIG. 9 is a diagram illustrating relative enhancement in fermentation rate for yeast cells in chromium depleted medium, and after addition of different concentrations of chromium ascorbate.

FIGS. 8 and 9 describe the fermentation rate, i.e., production by yeast cells under anaerobic conditions at 30° C., overtime, at different concentrations of chromium-ascorbate. Chromium axcorbate enhances the production of $CO_2$ thus indicating GTF activity.

Figure 10:
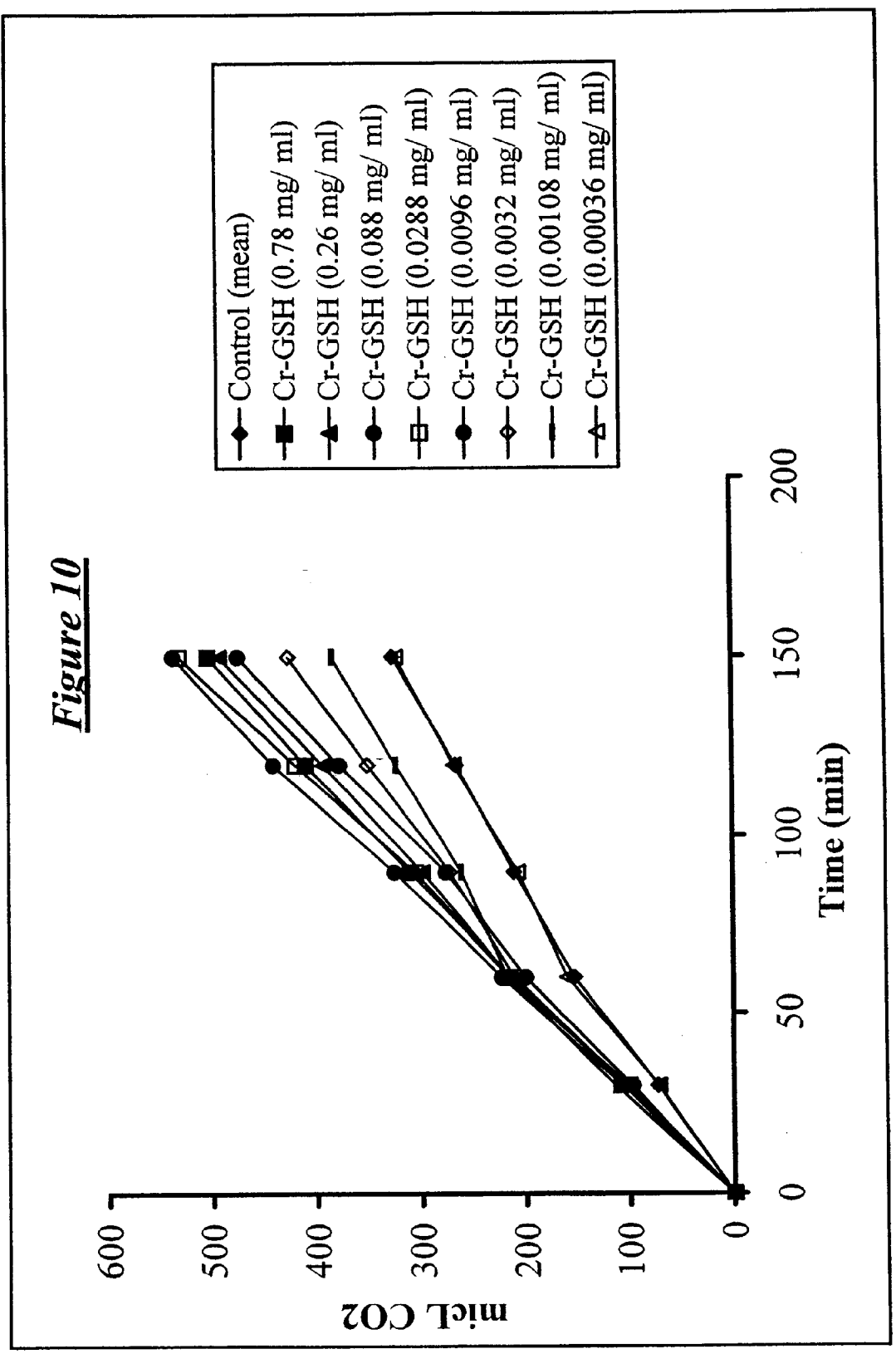
FIG. 10 is a diagram illustrating carbon dioxide production in yeast cells in chromium depleted medium and after addition of different concentrations of chromium glutathione.
Figure 11:
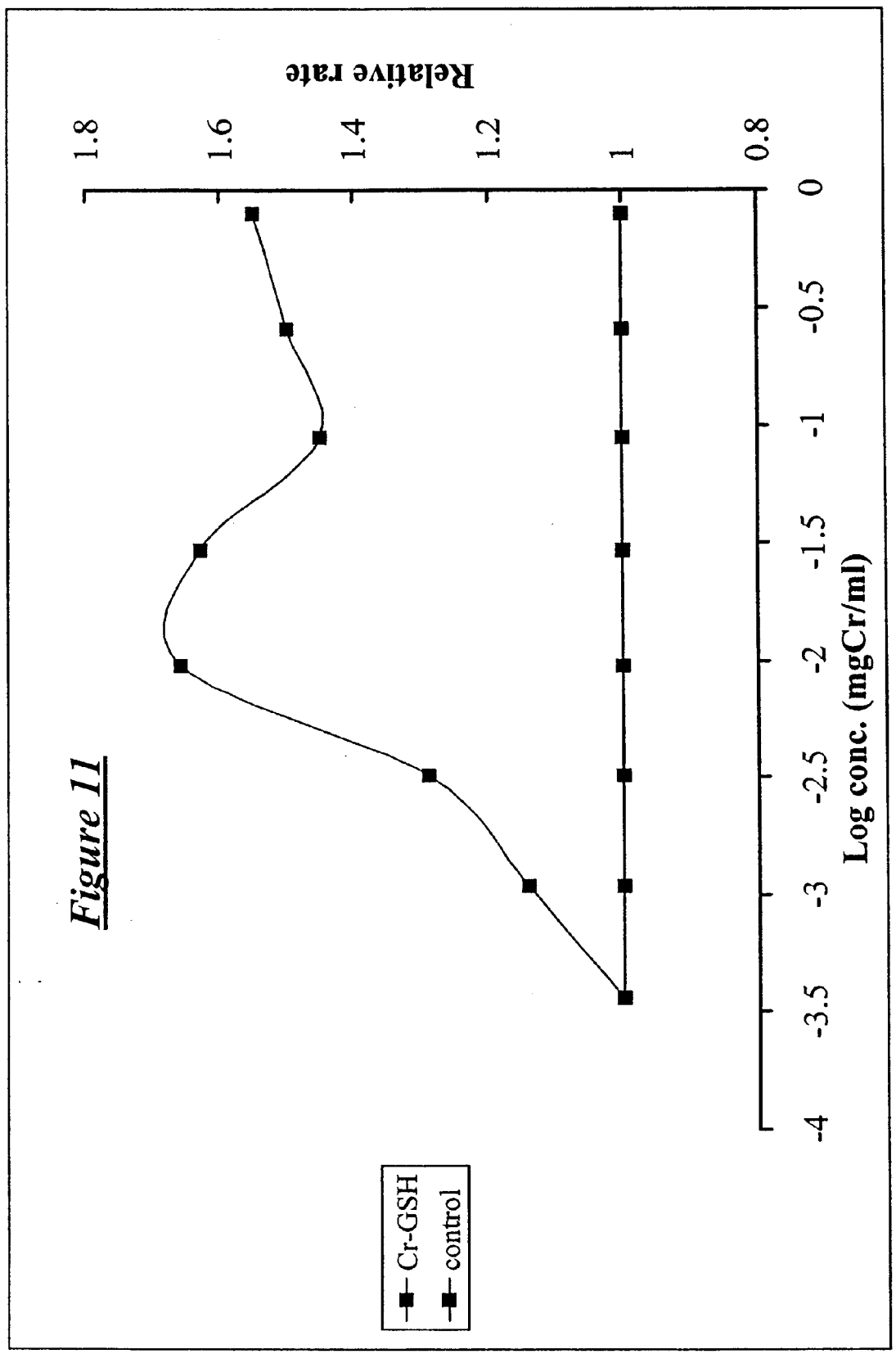
FIG. 11 is a diagram illustrating relative enhancement in fermentation rate for yeast cells in chromium depleted medium, and after addition of different concentrations chromium glutathione.

FIGS. 10 and 11 describe the fermentation rate, i.e., production by yeast cells under anaerobic conditions at 30° C., overtime, at different concentrations of chromium glutathione. Chromium glutathione increases the production of $CO_2$ thus indicating GTF activity.

Figure 12:
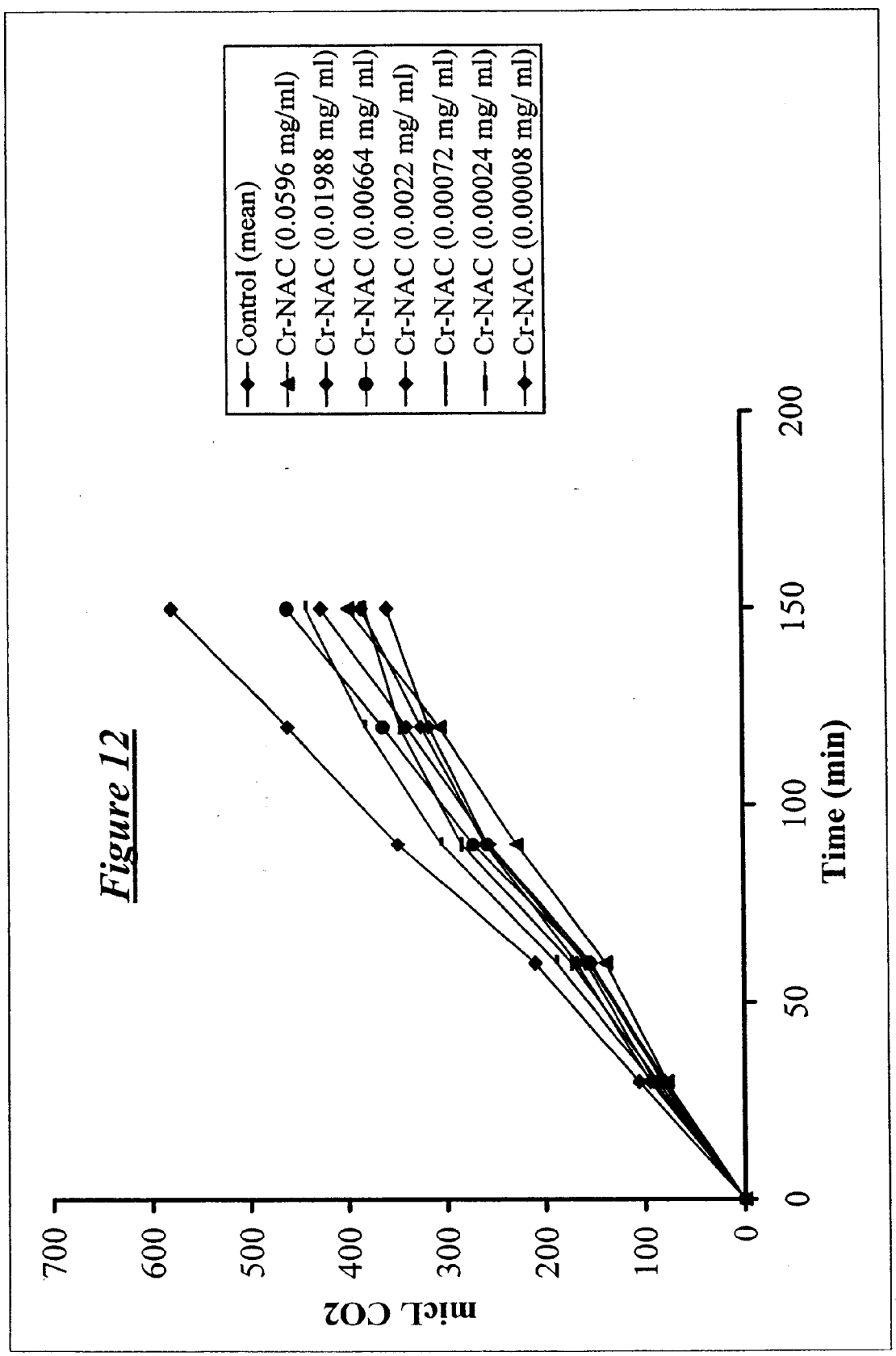
FIG. 12 is a diagram illustrating carbon dioxide production in yeast cells in chromium depleted medium and after addition of different concentrations of chromium N-acetyl cysteine.
Figure 13:
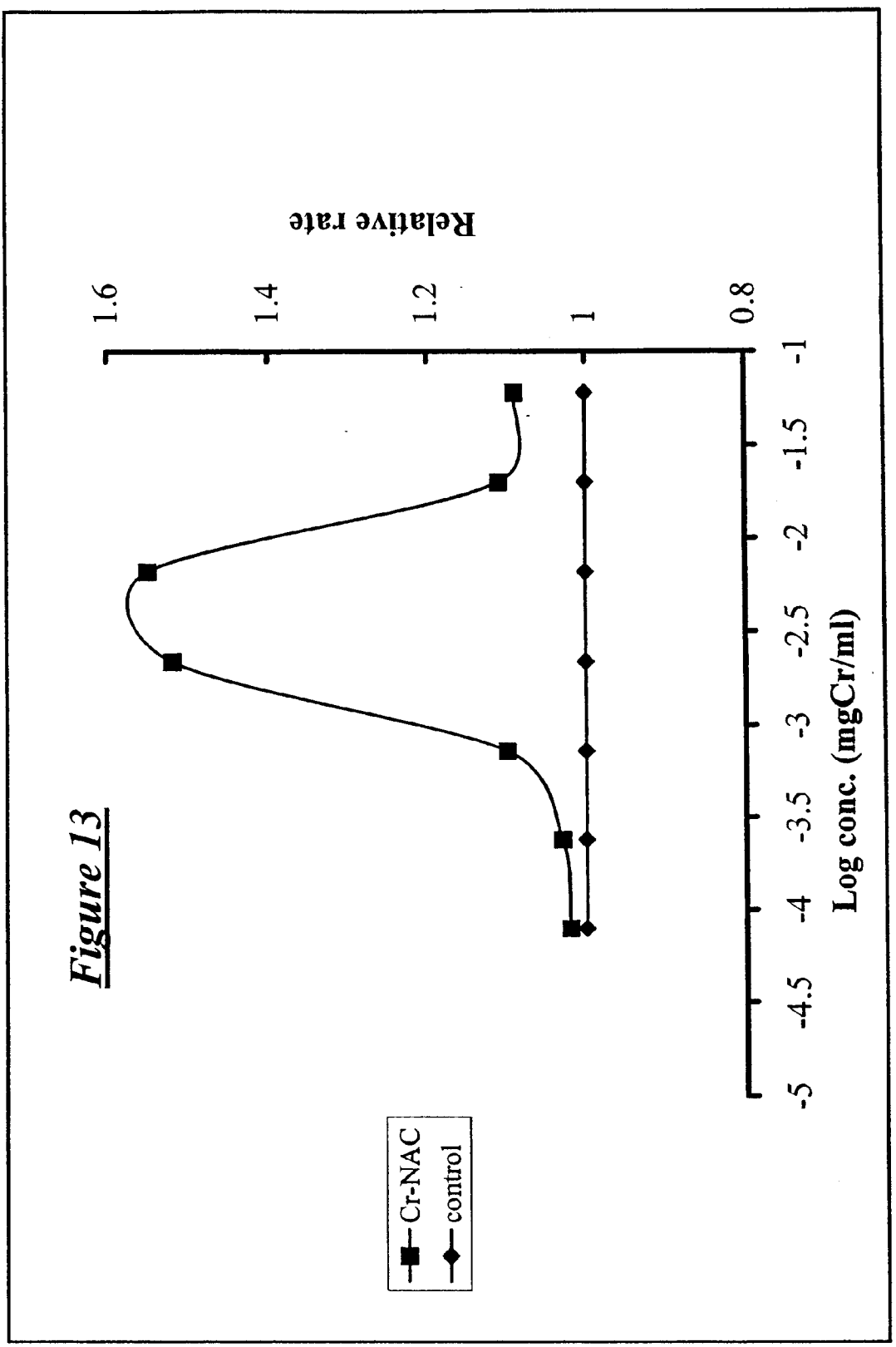
FIG. 13 is a diagram illustrating relative enhancement in fermentation rate for yeast cells in chromium depleted medium, and after addition of different concentrations of chromium N-acetyl cysteine.

FIGS. 12 and 13 describe the fermentation rate, i.e., production by yeast cells under anaerobic conditions at 30° C., overtime, at different concentrations of chromium-N-acetyl cysteine. Chromium-N-acetyl cysteine increases the production of $CO_2$ thus indicating GTF activity.

5.5 In vivo hypoglycemic effects of chromium compounds

5.5.1 Streptozotocin Rats - Model for type I Diabetes.

Sprague Dawly male rats weighing 120–130 g were injected subcutanously with a single dose of streptozotocin (60 mg/kg body weight) in 0.5 ml citrate buffer, 0.05 M pH 4.5. Plasma glucose concentrations were measured seven days later using commercial glucometer. Animals with blood glucose higher than 250 mg/dl were chosen for the subsequent test with fractions purified from yeast extract or the Saltbush, as described in section 5.1 and 5.2.

The chromium containing solutions (0.5 or 1.0 ml) were introduced orally in a dose of 200–300 ng Cr/animal. Blood was collected from the tail vein at intervals of 30 min, and levels of glucose, free fatty acids and triglycerides were measured as described previously. Mirsky, N. J. Inorg. Biochem. 49:123–128 (1993).

FIG. 14 describes glucose load in diabetic rats which receive a placebo dose or a single dose of 1 gr/rat of chromium containing partially purified fraction from yeast extract.

FIG. 15 describes glucose load in diabetic rats, which receive a placebo dose or a single dose of 0.25, 0.5 or 1.0 g/rat of 100% methanol eluate fraction from Saltbush.

Table 3 below describes the lipid levels in severely diabetic and mildly diabetic rats treated with chromium containing fractions extracted from yeast at 300 ng cr/dose/day for 30 days.

TABLE 3

Blood lipids concentration in control rats, diabetic and diabetic treated with 30 daily doses of yeast GTF (300 ng Cr/dose)

| | Triglycerides (mg/dl) | Total cholesterol (mg/dl) | HDL cholesterol (mg/dl) |
|---|---|---|---|
| Healthy control | 52 | 66.5 | 25.8 |
| Diabetic untreated | 206.4 | 84.7 | 18.9 |
| Diabetic + GTF | 61.6 | 82.8 | 25.9 |

5.5.2 Sand Rats and Spiny Mice - Models for type II Diabetes.

Sand rats (Psammomys obesus) and Spiny mice (Acomys rusatus), when fed high energy diet, develop diabetes type II. Schmidt-Nielsen K & Haines H B., Science 143: 689–690, (1964). These animals were used to examine the hypoglycemic activity of the chromium compounds. An oral glucose tolerance test with 2g glucose/kg body weight was performed in diabetic spiny mice (Acomys russatus) supplemented with a single dose of chromium containing natural extract at 200 ng Cr/animal.

FIG. 16 describes a remarkable improvement in glucose clearance in spiny mice following administration of chromium containing natural compositions from yeast.

FIG. 17 describes a remarkable improvement in glucose clearance, in the sand rat following administration of chromium containing natural compositions from yeast.

5.5.3 Effect of chromium containing natural compositions on insulin activity in diabetic rats When a marginal dose of insulin (0.005–0.025 mg /Kg body weight) was injected into streptozoatocin diabetic rats a decrease of 10–15% in blood glucose was observed after the injection. A single dose of active chromium fraction extraction from yeast decreased blood glucose by 15–20%. A combination of both insulin and chromium containing natural compound from yeast created much higher reduction in blood glucose of 40–45% reduction.

FIG. 18 describes the effect of chromium containing natural composition extracted from yeast on the activity of marginal levels of insulin in diabetes type I, in rats. These results indicate that the natural compositions extracted from yeast potentiate the insulin action in the rats.

5.5.4 Effect of chromium containing natural compositions in steroid-induced diabetes in rats.

Corticosteroid treatment often leads to impaired glucose tolerance and diabetes. Merck manual, $14^{th}$ edn. Rahway, N.J. : Merck Sharp and Dohme Research Laboratories, 1982, 2385. Steroid diabetes, similar to the syndrome of chromium deficiency, is characterized by insulin resistance in the absence of ketosis and acidosis.

FIG. 19 describes blood glucose load in diabetic rats which were either untreated or which given an oral single dose of chromium containing natural composition extracted from yeast. Diabetes was induced by steroid treatment for several days. A remarkable improvement of glucose tolerance is observed in animals supplemented with chromium containing natural composition extracted from yeast.

The present invention is not to be limited in scope by the embodiments disclosed in the examples which are intended as an illustration.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

What is claimed is:

1. A composition isolated from Saltbush having hypoglycemic or hypolipidemic activity, wherein said composition is prepared by a process comprising the steps of:
    (a) mixing water extracts obtained from Saltbush with a mixture of polar organic solvents selected from the group consisting of ethanol, methanol and acetonitrile, and a non polar organic solvent selected from the group consisting of butanol, chloroform and hexane, to produce a suspension;
    (b) allowing the suspension to first separate into a non-polar phase and a polar phase, and then collecting the polar phase;
    (c) subjecting the polar phase to an ethanol extraction, whereby an active eluate is collected; and
    (d) subjecting the active eluate from (c) to a methanol extraction to obtain an active eluant composition.

2. A purified composition isolated from Saltbush having hypoglycemic or hypolipidemic activity, wherein said composition is prepared by a process comprising the steps of
    (a) mixing water extracts obtained from Saltbush with a mixture of polar organic solvents selected from the group consisting of ethanol, methanol and acetonitrile, and a non polar organic solvent selected from the group consisting of butanol, chloroform and hexane, to produce a suspension;
    (b) allowing the suspension to first separate into a non-polar phase and a polar phase, and then collecting the polar phase;
    (c) subjecting the polar phase to an ethanol extraction, whereby an active eluate is collected; and,
    (d) subjecting the active eluate from step (c) to a methanol extraction to obtain an active eluant;
    (e) chromatagraphically separating the active eluant of step (d); and
    (f) obtaining a fraction which has a mass spectrum comprising peaks at 86, 120, 136, 241, 288, 399, 453, and 485 m/z.

3. A purified composition isolated from Saltbush having hypoglycemic or hypolipidemic activity, wherein said composition is prepared by a process comprising the steps of
    (a) mixing water extracts obtained from Saltbush with a mixture of polar organic solvents selected from the group consisting of ethanol, methanol and acetonitrile, and a non polar organic solvent selected from the group consisting of butanol, chloroform and hexane, to produce a suspension;
    (b) allowing the suspension to first separate into a non-polar phase and a polar phase, and then collecting the polar phase;
    (c) subjecting the polar phase to an ethanol extraction, whereby an active eluate is collected; and,
    (d) subjecting the active eluate from (c) to a methanol extraction to obtain an active eluant;
    (e) chromatagraphically separating the active eluant of step (d); and
    (f) obtaining a fraction which has a mass spectrum comprising peaks at 104, 118, 140, 156, 186, 235, 257, 273, 315, 374, and 432 m/z.

4. The composition according to claims 1, 2, or 3 further comprising of an antioxidant selected from the group consisting of vitamin C, vitamin E, reduced glutathione, manganese, beta-carotene, ergothionine, zinc, selenium, cysteine, N-acetyl cysteine, methionine, and 2-mercaptoethanol.

* * * * *